United States Patent
Patel

(10) Patent No.: US 10,017,809 B2
(45) Date of Patent: *Jul. 10, 2018

(54) NUCLEIC ACID AMPLIFICATION

(71) Applicant: Theranos IP Company, LLC, Newark, CA (US)

(72) Inventor: Pranav Patel, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 15/152,997

(22) Filed: May 12, 2016

(65) Prior Publication Data

US 2016/0281155 A1 Sep. 29, 2016

Related U.S. Application Data

(63) Continuation of application No. 14/214,848, filed on Mar. 15, 2014, now Pat. No. 9,416,387.

(60) Provisional application No. 61/800,340, filed on Mar. 15, 2013.

(51) Int. Cl.
*C12Q 1/68* (2018.01)
*C12Q 1/6855* (2018.01)
*C12P 19/34* (2006.01)
*C12Q 1/6844* (2018.01)

(52) U.S. Cl.
CPC ............ *C12Q 1/6855* (2013.01); *C12P 19/34* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 5,714,320 A * | 2/1998 | Kool | C12N 15/10 435/5 |
| 5,834,252 A | 11/1998 | Stemmer et al. | |
| 5,874,260 A | 2/1999 | Cleuziat et al. | |
| 5,928,905 A | 7/1999 | Stemmer et al. | |
| 6,033,881 A | 3/2000 | Himmler et al. | |
| 6,090,552 A | 7/2000 | Nazarenko et al. | |
| 6,194,179 B1 | 2/2001 | Werner et al. | |
| 6,235,502 B1 | 5/2001 | Weissman et al. | |
| 6,620,597 B1 | 9/2003 | Chen et al. | |
| 6,743,605 B1 | 6/2004 | Rabbani et al. | |
| 6,764,821 B1 | 7/2004 | Rabbani et al. | |
| 6,916,634 B2 | 7/2005 | Kopreski | |
| 6,977,148 B2 | 12/2005 | Dean et al. | |
| 6,977,153 B2 * | 12/2005 | Kumar | C12N 15/1096 435/6.12 |
| 7,264,930 B2 | 9/2007 | Rabbani et al. | |
| 7,297,485 B2 | 11/2007 | Bornarth et al. | |
| 7,468,245 B2 | 12/2008 | Rabbani et al. | |
| 7,485,417 B2 | 2/2009 | Rabbani et al. | |
| 7,713,691 B2 | 5/2010 | Rabbani et al. | |
| 7,803,579 B2 | 9/2010 | Mitani et al. | |
| 7,955,795 B2 | 6/2011 | Kumar | |
| 7,993,839 B2 | 8/2011 | Nelson et al. | |
| 8,133,989 B2 | 3/2012 | Rabbani et al. | |
| 8,206,902 B2 | 6/2012 | Mitani et al. | |
| 8,236,499 B2 | 8/2012 | Patel et al. | |
| 8,288,092 B2 | 10/2012 | Rabbani et al. | |
| 8,420,323 B2 | 4/2013 | Miyoshi et al. | |
| 8,435,741 B2 | 5/2013 | Miyoshi et al. | |
| 8,445,664 B2 | 5/2013 | Rabbani et al. | |
| 8,486,633 B2 | 7/2013 | Rabbani et al. | |
| 8,709,724 B2 | 4/2014 | Tabor et al. | |
| 2001/0049125 A1 | 12/2001 | Stemmer et al. | |
| 2003/0032016 A1 | 2/2003 | Barany et al. | |
| 2004/0170968 A1 | 9/2004 | Lizardi | |
| 2004/0209272 A1 | 10/2004 | Ben-Asouli et al. | |
| 2005/0037393 A1 | 2/2005 | Gunderson et al. | |
| 2005/0074804 A1 * | 4/2005 | Wang | C12N 15/1096 435/6.12 |
| 2005/0084894 A1 | 4/2005 | Brow et al. | |
| 2005/0112631 A1 | 5/2005 | Piepenburg et al. | |
| 2005/0202490 A1 | 9/2005 | Makarov et al. | |
| 2005/0277146 A1 | 12/2005 | Shigemori et al. | |
| 2006/0040300 A1 | 2/2006 | Dapprich et al. | |
| 2006/0188893 A1 | 8/2006 | Kumar et al. | |
| 2006/0194214 A1 | 8/2006 | Church et al. | |
| 2007/0031857 A1 | 2/2007 | Makarov et al. | |
| 2007/0054301 A1 | 3/2007 | Becker et al. | |
| 2007/0128635 A1 | 6/2007 | Macevicz | |
| 2007/0141048 A1 | 6/2007 | Oleksiewicz et al. | |
| 2008/0227160 A1 | 9/2008 | Kool | |
| 2008/0305535 A1 | 12/2008 | Auerbach | |

(Continued)

FOREIGN PATENT DOCUMENTS

| CA | 1340121 E | 11/1998 |
|---|---|---|
| CN | 101906488 A | 12/2010 |

(Continued)

OTHER PUBLICATIONS

Office Action dated Oct. 19, 2017 for U.S. Appl. No. 14/850,697.
Prithiviraj et al. Rapid detection of microbial DNA by a novel isothermal genome exponential amplification reaction (GEAR) assay, Biochemical and Biophysical Research Communications, vol. 420, No. 4, Mar. 12, 2012, pp. 738-742.
Xu et al. Cross Priming Amplification: Mechanism and Optimization for Isothermal DNA Amplification, Scientific Reports, vol. 2, Feb. 2, 2012.
Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.
Sharbati-Tehrani et al. Concatameric cloning of porcine microRNA molecules after assembly PCR. Biochemical and Biophysical Research Communications, Elsevier, Amsterdam, NL, vol. 375, No. 3, Oct. 24, 2008, pp. 484-489.

(Continued)

*Primary Examiner* — Aaron A Priest

(57) ABSTRACT

Methods and compositions for the amplification of nucleic acids are disclosed. Amplification methods provided herein may be performed under isothermal conditions. Methods and compositions may include reagents such as restriction enzymes, polymerases, ligases, primers, and polynucleotide adaptors.

19 Claims, 7 Drawing Sheets

(56) References Cited

U.S. PATENT DOCUMENTS

| | | | |
|---|---|---|---|
| 2009/0098566 A1 | 4/2009 | Notomi et al. | |
| 2009/0098612 A1 | 4/2009 | Rhee et al. | |
| 2009/0143235 A1 | 6/2009 | Drmanac et al. | |
| 2009/0155856 A1 | 6/2009 | Miyoshi et al. | |
| 2009/0170096 A1 | 7/2009 | Miyoshi et al. | |
| 2009/0233277 A1 | 9/2009 | Murakami | |
| 2010/0029505 A1* | 2/2010 | Payan | C12N 15/1093 506/10 |
| 2010/0075384 A1 | 3/2010 | Kong et al. | |
| 2010/0151471 A1 | 6/2010 | Faham et al. | |
| 2010/0184154 A1 | 7/2010 | Miyoshi et al. | |
| 2011/0123991 A1 | 5/2011 | Hoser | |
| 2012/0157326 A1 | 6/2012 | Tisi et al. | |
| 2012/0315642 A1 | 12/2012 | Kankia | |
| 2012/0322666 A1* | 12/2012 | Pham | C12Q 1/6869 506/2 |
| 2013/0005585 A1 | 1/2013 | Anderson et al. | |
| 2013/0296535 A1 | 11/2013 | Church et al. | |
| 2013/0330722 A1* | 12/2013 | Miller | C12N 15/1003 435/6.11 |
| 2014/0113839 A1 | 4/2014 | Wu et al. | |
| 2014/0295439 A1 | 10/2014 | Patel | |
| 2014/0295440 A1 | 10/2014 | Belhocine et al. | |
| 2014/0295447 A1 | 10/2014 | Hayashizaki et al. | |
| 2014/0295498 A1* | 10/2014 | Turner | C12Q 1/6853 435/91.2 |
| 2014/0302504 A1 | 10/2014 | Belhocine et al. | |
| 2014/0329282 A1* | 11/2014 | Nelson | C12Q 1/6855 435/91.2 |
| 2014/0364764 A1 | 12/2014 | Jung et al. | |
| 2015/0140567 A1 | 5/2015 | Belhocine et al. | |
| 2016/0032357 A1 | 2/2016 | Barany et al. | |
| 2016/0060673 A1 | 3/2016 | Belhocine et al. | |
| 2016/0060674 A1 | 3/2016 | Patel | |
| 2016/0068895 A1 | 3/2016 | Belhocine et al. | |
| 2016/0076069 A1 | 3/2016 | Belhocine et al. | |
| 2016/0376647 A1* | 12/2016 | Travers | C12Q 1/6869 506/2 |

FOREIGN PATENT DOCUMENTS

| | | |
|---|---|---|
| EP | 0833942 B1 | 8/2000 |
| EP | 2048248 A1 | 4/2009 |
| EP | 0971039 B1 | 3/2011 |
| EP | 2692870 A1 | 2/2014 |
| GB | 2332516 A | 6/1999 |
| JP | 04131099 | 5/1992 |
| JP | 07016094 | 1/1995 |
| JP | 07067646 A2 | 3/1995 |
| WO | 1992001813 A1 | 2/1992 |
| WO | 1994003624 A1 | 2/1994 |
| WO | 1996001327 A1 | 1/1996 |
| WO | 1997004131 A1 | 2/1997 |
| WO | 2000079009 A2 | 12/2000 |
| WO | 02068683 A2 | 9/2002 |
| WO | 03072805 A2 | 9/2003 |
| WO | 2004061119 A2 | 7/2004 |
| WO | 2004070053 A2 | 8/2004 |
| WO | 2005030983 A2 | 4/2005 |
| WO | 2005059178 A1 | 6/2005 |
| WO | 2006095169 A1 | 9/2006 |
| WO | 2006119066 A2 | 11/2006 |
| WO | 2008012529 A1 | 1/2008 |
| WO | 2008032058 A2 | 3/2008 |
| WO | 2009120374 A2 | 10/2009 |
| WO | 2010117817 A2 | 10/2010 |
| WO | 2012017210 A1 | 2/2012 |
| WO | 2013003585 A2 | 1/2013 |
| WO | 2013035875 A1 | 3/2013 |
| WO | 2014025337 A1 | 2/2014 |

OTHER PUBLICATIONS

Ashford. PATH using TwistDx's Amplification Tech in Minimally Instrumented HIV Test for Infants, GenomeWeb, Aug. 25, 2011.
Dean et al. Rapid Amplification of Plasmid and Phase DNA Using Phi29 DNA Polymerase and Multiply-Primed Rolling Circle Amplification.
Euler et al. Recombinase polymerase amplification assay for rapid detection of Rift Valley fever virus. J Clin Virol. Aug. 2012;54(4):308-12. Epub Jun. 9, 2012.
G.J Hafner, et al. Isothermal Amplification and Multimerization of DNA by Bst DNA Polymerase. BioTechniques 30:852-867; Apr. 2001.
International Search Report and Written Opinion dated Aug. 14, 2014 for Application No. PCT/US2014/030028.
International Search Report and Written Opinion dated Aug. 14, 2014 for Application No. PCT/US2014/030036.
International Search Report and Written Opinion dated Sep. 18, 2014 for PCT/US2014/030034.
Lee et al. Versatile PCR-mediated insertion or deletion mutagenesis.
Merriam-Webster, definition of "analogous", available at http://www.merriam-webster.com/dictionary/analogous, accessed May 18, 2015.
Merriam-Webster, definition of "partner", available at http://www.merriam-webster.com/dictionary/partner, accessed May 18, 2015.
Merriam-Webster, definition of "portion", available at http://www.merriam-webster.com/dictionary/portion, accessed May 18, 2015.
Merriam-Webster, definition of "represent", available at http://www.merriam-webster.com/dictionary/represent, accessed May 18, 2015.
Notice of Allowance dated Mar. 4, 2016 for U.S. Appl. No. 14/214,848.
Notomi et al. Loop-medicated isothermal amplification of DNA, Nucleic Acids Res. Jun. 15, 2000;28(12):E63.
Office Action dated Oct. 26, 2015 for U.S. Appl. No. 14/546,998.
Office Action dated Oct. 30, 2015 for U.S. Appl. No. 14/214,848.
Office Action dated May 11, 2016 for U.S. Appl. No. 14/546,998.
Office Action dated Jun. 8, 2015 for U.S. Appl. No. 14/546,998.
Ohshima K and Wells RD. Hairpin formation during DNA synthesis primer realignment in vitro in triplet repeat sequences from human hereditary disease genes. Journal of Biological Chemistry 272:16798-16806; Jul. 1997.
Patel R et al. Formation of chimeric DNA primer extension products by template switching onto an annealed downstream oligonucleotide. PNAS 93:2969-2974; Apr. 1996.
Rohrman et al. A Paper and Plastic Device for Performing Recombinase Polymerase Amplification of HIV DNA. Lab Chip, Sep. 7, 2012;12(17):3082-8. Epub Jun. 26, 2012.
Wang et al. Rolling circle amplification-mediated hairpin RNA (RMHR) library construction in plants.
Wilton SD et al. Snapback SSCP analysis: Engineered conformation changes for the rapid typing of known mutations. Human Mutation 11:252-258; Mar. 1998.
Written Opinion and International Search Report dated Dec. 25, 2014 for PCT/US2014/056151.
Fire et al. Rolling replication of short DNA circles, Proceedings of the National Academy of Sciences, National Academy of Sciences, US, vol. 92, No. 10, May 1995.
Liu et al. Rolling Circle DNA Synthesis: Small Circular Oligonucleotides as Efficient Templates for DNA Polymerases, Journal of the American Chemical Society, American Chemical Society, US, vol. 118, No. 7, 1996.
Lizardi et al. Mutation detection and single-molecule counting using isothermal rolling-circle amplification, Nature Genetics, Nature Publishing Group, New York, US, vol. 19, No. 3, Jul. 1998.
Marciniak et al. Coupled rolling circle amplification loop-mediated amplification for rapid detection of short DNA sequences, Biotechniques, 2008, 45:275-280.
Notice of Allowance dated Sep. 7, 2016 for U.S. Appl. No. 14/546,998.
Office Action dated Nov. 25, 2016 for U.S. Appl. No. 14/214,854.
Office Action dated Jul. 6, 2016 for U.S. Appl. No. 14/546,998.
Office Action dated Sep. 27, 2016 for U.S. Appl. No. 14/214,850.

(56) References Cited

OTHER PUBLICATIONS

White et al. Concatemer Chain Reaction: a Taq DNA Polymerase-Mediated Mechanism for Generating Long Tandemly Repetitive DNA Sequences. Analytical Biochemistry, Academic Press Inc, New York, vol. 199, No. 2, Dec. 1, 1991, pp. 184-190.

\* cited by examiner

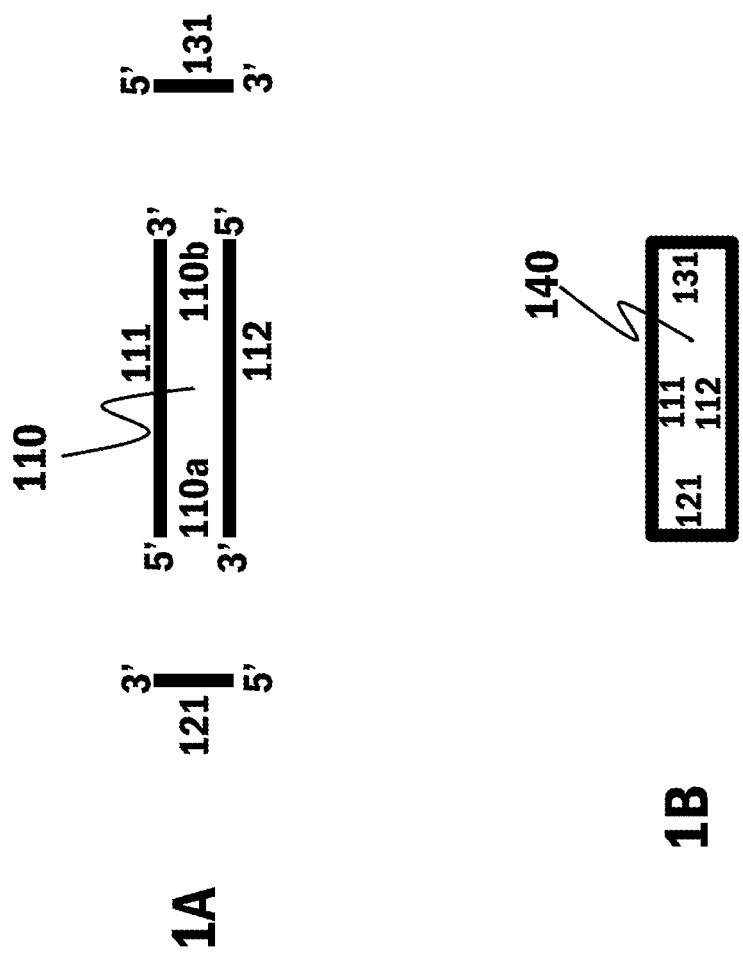

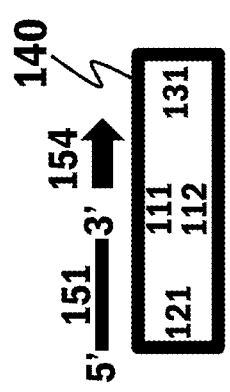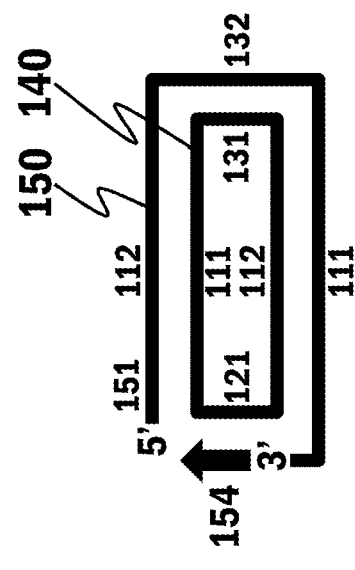
Fig. 1 - Continued

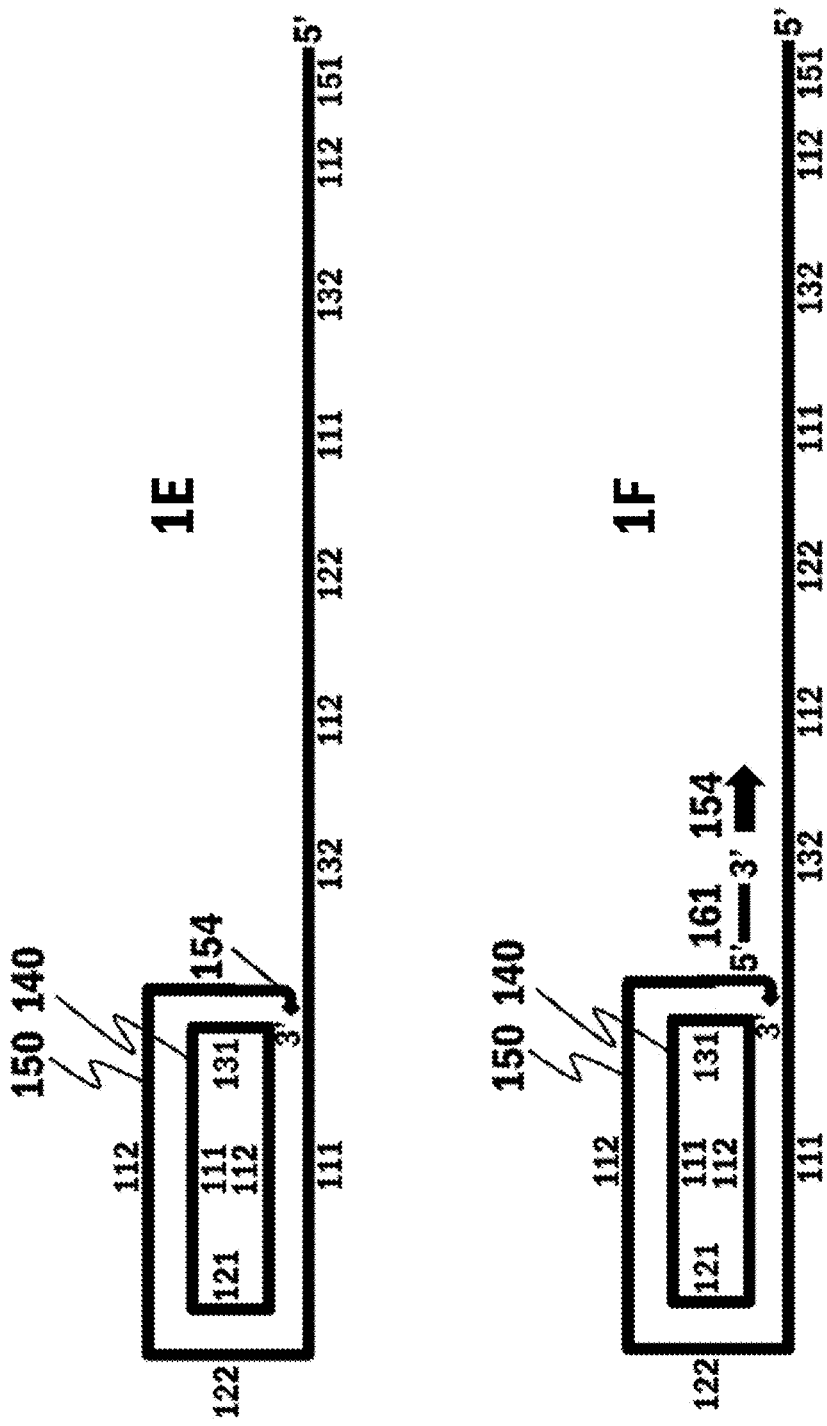
Fig. 1 - Continued

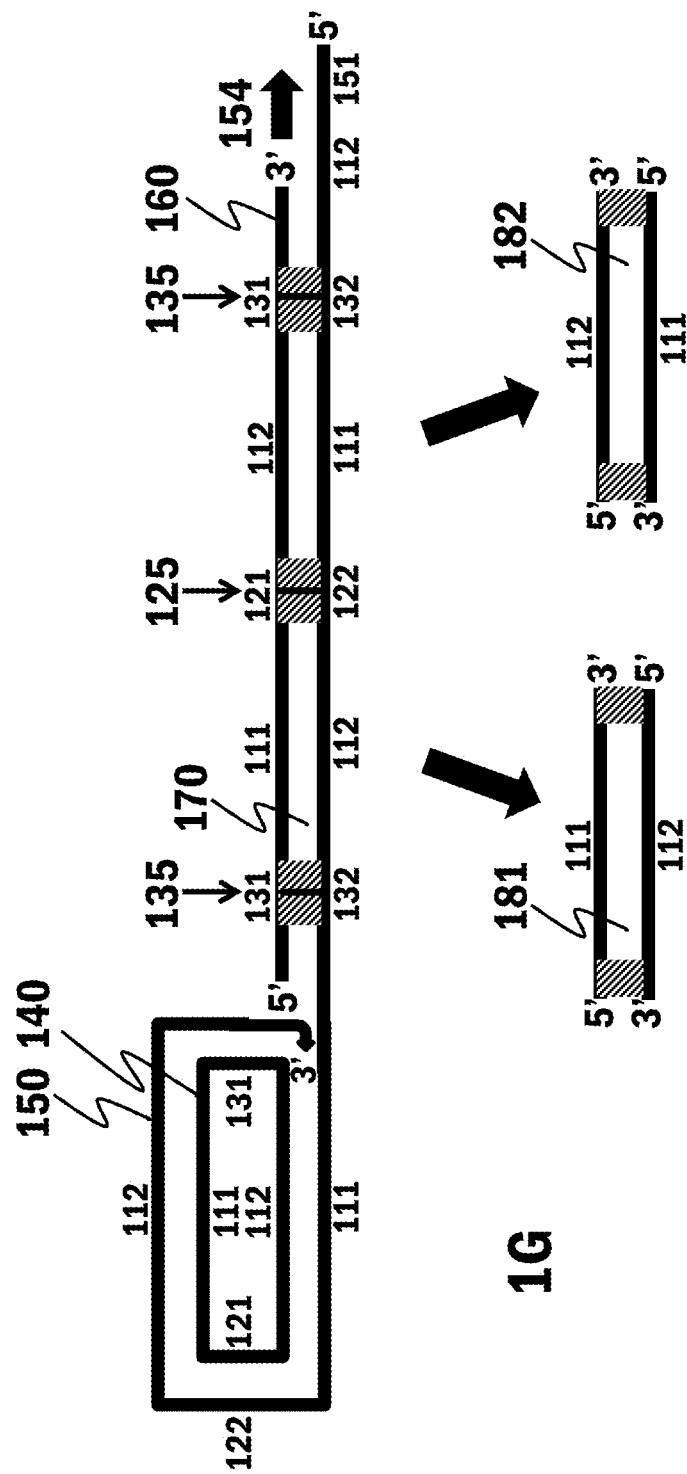
Fig. 1 - Continued

NUCLEIC ACID AMPLIFICATION

CROSS-REFERENCE TO RELATED APPLICATIONS

This application is a continuation of U.S. application Ser. No. 14/214,848, filed Mar. 15, 2014, which claims the benefit of, and priority to U.S. Provisional Patent Application No. 61/800,340, filed Mar. 15, 2013, both of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on May 28, 2014, is named 2025.201_SL.txt and is 12,247 bytes in size.

BACKGROUND

There is an increasing need for methods and reagents for the amplification of nucleic acids. Generation of multiple copies of a particular nucleic acid is often necessary or helpful in order for the nucleic acid to be used for a given application. For example, in order to analyze the nucleotide sequence of a nucleic acid of interest, frequently, the nucleic acid is replicated to increase its copy number before the sequence is analyzed. In another example, in order to determine the presence or absence of a particular nucleic acid in a sample, a sample may be treated under conditions such that if the particular nucleic acid is present in the sample, it may be amplified. In another example, a nucleic acid for use as probe may be copied repeatedly to generate a large number of nucleic acids containing the same sequence as the original nucleic acid template, thereby generating many copies of the nucleic acid which may be used as a probe.

A variety of methods for the amplification of nucleic acids are known. For example, polymerase chain reaction ("PCR") (see, e.g. U.S. Pat. No. 4,683,202) is a popular method for the amplification of nucleic acids. To successfully perform a PCR reaction, the reaction must be performed at multiple different temperatures. This requires hardware or other mechanisms for repeatedly changing the temperature of the PCR reaction. Another method for amplification of nucleic acids is referred to as loop-mediated isothermal amplification ("LAMP") (see, e.g. U.S. Pat. No. 6,410,278). LAMP reactions may be performed isothermally, but typically involve the use of four different primers which recognize a total of six distinct sequences on the target nucleic acid.

To facilitate the generation of amplified nucleic acids for the many and growing number of applications which use amplified nucleic acids, new methods and reagents for the amplification of nucleic acids are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein are methods and compositions relating to the amplification of nucleic acids.

In some embodiments, provided herein is a method for amplifying a linear double-stranded nucleic acid template comprising two separate complementary strands, comprising: (A) generating a circular strand from the linear double-stranded nucleic acid template, wherein the circular strand comprises the single-strand component of at least one restriction enzyme recognition sequence and the sequences of each of the two separate complementary strands; (B) treating the circular strand with a first oligonucleotide primer and a polymerase, under conditions such that an extension product of the first primer is synthesized; (C) treating the extension product of the first primer of step (B) with a second oligonucleotide primer and a polymerase, under conditions such that an extension product of the second primer is synthesized which is complementary to the extension product of the first primer of step (B), to produce a new double-stranded nucleic acid comprising at least a portion of the extension product of the first primer and at least a portion of the extension product of the second primer; and (D) treating the new double-stranded nucleic acid of step (C) with a restriction enzyme that recognizes a full double-stranded restriction enzyme recognition sequence corresponding to the at least one restriction enzyme recognition sequence of step (A), under conditions such that the new double-stranded nucleic acid of step (C) is cleaved to form two or more shorter double-stranded nucleic acids, at least two of which comprise at least a portion of a copy of the linear double-stranded nucleic acid template of step (A), thereby amplifying the linear double-stranded nucleic acid template.

In some embodiments, provided herein is a method for amplifying a linear double-stranded nucleic acid template comprising two separate complementary strands, comprising: (A) treating the linear double-stranded nucleic acid template with two polynucleotide adaptors under conditions such that a circular strand comprising the two adaptors and the two complementary strands is formed, wherein each adaptor comprises a single nucleic acid strand which contains the single strand component of a restriction enzyme recognition sequence and which is configured to, under certain conditions, adopt a stem-loop structure; (B) treating the circular strand of step (A) with a first oligonucleotide primer and a polymerase, under conditions such that an extension product of the first primer is synthesized; (C) treating the extension product of the first primer of step (B) with a second oligonucleotide primer and a polymerase, under conditions such that an extension product of the second primer is synthesized which is complementary to the extension product of the first primer of step (B), to produce a new double-stranded nucleic acid comprising at least a portion of the extension product of the first primer and at least a portion of the extension product of the second primer; and (D) treating the new double-stranded nucleic acid from step (C) with a restriction enzyme that recognizes a full double-stranded restriction enzyme recognition sequence corresponding to a single strand component of a restriction enzyme sequence of step (A), under conditions such that the new double-stranded nucleic acid from step (C) is cleaved to form two or more shorter double-stranded nucleic acids, at least two of which comprise at least a portion of a copy of the linear double-stranded nucleic acid template of step (A), thereby amplifying the linear double-stranded nucleic acid template.

In some embodiments, provided herein is method for amplifying a linear double-stranded nucleic acid template, comprising: (A) treating a linear double-stranded nucleic acid template comprising two complementary strands and a first and second end with a first and a second polynucleotide adaptor, under conditions such that: i) the first adaptor is ligated to the termini of both complementary strands present at the first end of the linear double-stranded nucleic acid template, ii) the second adaptor is ligated to the termini of both complementary strands present at the second end of the linear double-stranded nucleic acid, and iii) a circular strand comprising the two adaptors and the two complementary strands is formed, wherein each adaptor: i) comprises a single nucleic acid strand which contains the single strand component of a restriction enzyme recognition sequence and ii) is configured to, under certain conditions, adopt a stem-loop structure; (B) treating the circular strand of step (A) with a first oligonucleotide primer and a polymerase, under conditions such that an extension product of the first primer is synthesized; (C) treating the extension product of the first primer of step (B) with a second oligonucleotide primer and a polymerase, under conditions such that an extension product of the second primer is synthesized which is complementary to the extension product of the first primer of step (B), to produce a new double-stranded nucleic acid comprising at least a portion of the extension product of the first primer and at least a portion of the extension product of the second primer; and (D) treating the new double-stranded nucleic acid from step (C) with a restriction enzyme that recognizes a full double-stranded restriction enzyme recognition sequence corresponding to the single strand component of a restriction enzyme sequence of at least one of the adaptors, under conditions such that the new double-stranded nucleic acid from step (C) is cleaved to form two or more shorter double-stranded nucleic acids, at least two of which comprise at least a portion of a copy of the linear double-stranded nucleic acid template of step (A), thereby amplifying the linear double-stranded nucleic acid template.

In some embodiments, provided herein is a method for amplifying a linear double-stranded nucleic acid template comprising two separate complementary strands, comprising: (A) ligating an adaptor comprising a single nucleic acid strand to each end of a linear double-stranded nucleic acid template, to yield a circular strand containing the general formula in the 5' to 3' direction: -A1-S1-A2-S2-, wherein each adaptor contains at least four nucleotide bases and a single strand component of a restriction enzyme recognition sequence, A1 and A2 denote separate adaptors, S1 denotes a first complementary strand of the linear double-stranded nucleic acid template, S2 denotes a second complementary strand of the linear double-stranded nucleic acid template, the 3' terminus of A1 is ligated to the 5' terminus of S1, the 3' terminus of S1 is ligated to the 5' terminus of A2, the 3' terminus of A2 is ligated to the 5' terminus of S2, and the 3' terminus of S2 is ligated to the 5' terminus of A1; (B) annealing a first oligonucleotide primer to the circular strand; (C) extending the first oligonucleotide primer along the circular strand by using a polymerase, to form an extension product of the first primer; (D) annealing a second oligonucleotide primer to the extension product of the first primer; (E) extending the second oligonucleotide primer along at least a portion of the extension product of the first primer by using a polymerase, to produce a new double-stranded nucleic acid comprising at least a portion of the extension product of the first primer and at least a portion of the extension product of the second primer; and (F) cleaving the new double-stranded nucleic acid of step with a restriction enzyme that recognizes a full double-stranded restriction enzyme recognition sequence corresponding to the single strand component of a restriction enzyme sequence of at least one of the adaptors, to form two or more shorter double-stranded nucleic acids, at least two of which comprise at least a portion of a copy of the linear double-stranded nucleic acid template of step (A), thereby amplifying the linear double-stranded nucleic acid template.

In some embodiments, provided herein is a method for amplifying a linear double-stranded nucleic acid template, comprising: (A) preparing a reaction mixture comprising: (i) the linear double-stranded nucleic acid template comprising a first complementary strand and a second complementary strand, (ii) an isolated nucleic acid ligase, (iii) an isolated nucleic acid polymerase, and (iv) an isolated restriction enzyme; and (B) incubating the reaction mixture for at least 3 minutes.

In some embodiments, provided herein is a vessel, comprising in fluidic communication therein: (A) an isolated nucleic acid ligase, (B) an isolated nucleic acid polymerase, (C) an isolated restriction enzyme, and (D) a polynucleotide adaptor, wherein the adaptor comprises a single nucleic acid strand which contains the single strand component of a restriction enzyme recognition sequence and which is configured to, under certain conditions, adopt a stem-loop structure.

In some embodiments, provided herein is a kit for detecting a target nucleic acid of interest, the kit comprising two or more fluidically isolated containers, the containers collectively comprising: (A) an isolated nucleic acid ligase, (B) an isolated nucleic acid polymerase, (C) an isolated restriction enzyme, and (D) a polynucleotide adaptor, wherein the adaptor comprises a single nucleic acid strand which contains the single strand component of a restriction enzyme recognition sequence and which is configured to, under certain conditions, adopt a stem-loop structure.

In some embodiments, in a method provided herein comprising amplifying a linear double-stranded nucleic acid template through a process involving the generation of shorter double-stranded nucleic acids, the method may be repeated for 1, 2, 3, 4, 5, 10, 15, 20, 25, 50, 100, or more cycles, wherein a shorter double-stranded nucleic acid from one cycle of the method is used as a linear double-stranded nucleic acid template in another cycle of the method.

In some embodiments, a composition provided above or elsewhere herein comprising an isolated nucleic acid ligase, an isolated nucleic acid polymerase, and an isolated restriction enzyme, may further comprise an isolated reverse transcriptase enzyme.

In some embodiments, in a composition or method provided above or elsewhere herein involving amplification of a linear double-stranded nucleic acid template, the method may comprise generating concatemer comprising two or more copies of the linear double-stranded nucleic acid template.

In some embodiments, in a composition or method provided above or elsewhere herein involving amplification of a linear double-stranded nucleic acid template and generating a concatemer comprising two or more copies of the linear double-stranded nucleic acid template, the method may comprise cleaving the concatemer with a restriction enzyme to generate two or more shorter double-stranded nucleic acids containing at least a portion of a copy of the linear double-stranded nucleic acid template.

In some embodiments, in a composition or method provided above or elsewhere herein involving adaptor comprising a single nucleic acid strand which contains the single strand component of a restriction enzyme recognition sequence and which is configured to, under certain conditions, adopt a stem-loop structure, the stem of the stem-loop structure comprises the 5' and 3' terminal nucleotides of the adaptor, and 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more nucleotides downstream or upstream of the 5' or 3' terminal nucleotides, respectively.

In some embodiments, in a composition or method provided above or elsewhere herein involving adaptor comprising a single nucleic acid strand which contains the single strand component of a restriction enzyme recognition sequence and which is configured to, under certain conditions, adopt a stem-loop structure, the single nucleic acid strand comprises a 5' region, a middle region, and a 3' region, the 5' region and 3' region are complementary to each other, and the 5' region and 3' region, when annealed to each other, form the stem of the stem-loop structure.

In some embodiments, in a composition or method provided above or elsewhere herein involving an adaptor having a stem-loop structure, the stem of the stem-loop structure comprises the 5' and 3' terminal nucleotides of the adaptor, and comprises an outermost region and inner region, wherein the outermost region of the stem comprises the 5' and 3' terminal nucleotides of the adaptor.

In some embodiments, in a method provided above or elsewhere herein involving amplifying a linear double-stranded nucleic acid template, the method comprises preparing a reaction mixture containing reagents for performing the method. In some embodiments, a reaction mixture may be prepared in or placed in a vessel.

In some embodiments, in a method provided above or elsewhere herein involving preparing a reaction mixture containing reagents for performing the method, the reaction mixture may be incubated at a constant temperature. The reaction mixture may be incubated at a constant temperature for at least 1, 2, 3, 4, 5, 10, 15, 20, 25, 30, 40, 50, 60, 90, 120, or 180 minutes. The reaction mixture may be incubated at a constant temperature of no greater than 90, 85, 80, 75, 70, 65, 60, 55, 50, 45, 40, 35, 30, 25, 20, 15, or 10 C.

In some embodiments, in a method provided above or elsewhere herein involving generating a shorter double-stranded nucleic acid from the cleavage of a new double-stranded nucleic acid, the shorter double-stranded nucleic acid generated in a first cycle of the method may be used as the linear double-stranded nucleic acid template in a second cycle of the method.

In some embodiments, in a method provided above or elsewhere herein involving generating two or more shorter double-stranded nucleic acid from the cleavage of a new double-stranded nucleic acid, at least two of the two or more shorter double-stranded nucleic acids contain a complete copy of a linear double-stranded nucleic acid template used in the method as starting material to generate the shorter double-stranded nucleic acids.

In some embodiments, in a method provided above or elsewhere herein involving cleaving a new double-stranded nucleic acid to generate one or more shorter double-stranded nucleic acids, the new double-stranded nucleic acid is cleaved by a restriction enzyme which recognizes a full double-stranded restriction enzyme recognition sequence in the new double-stranded nucleic acid.

In some embodiments, in a method provided above or elsewhere herein involving amplification of a linear double-stranded nucleic acid template, the number of copies of the linear double-stranded nucleic acid template at least doubles every 0.1, 0.5, 1, 2, 3, 4, 5, 10, 15, 20, 25, 30, 35, 40, 45, 50, 55, 60, 70, 80, 90, 100, 110, 120, 150, 180, or 240 minutes of the method.

In some embodiments, in a method provided above or elsewhere herein involving amplification of a linear double-stranded nucleic acid template, the method further comprises generating the linear double-stranded nucleic acid template for amplification from a single strand nucleic acid target molecule. In some embodiments, the single strand nucleic acid target molecule may be a single strand DNA or RNA molecule. In some embodiments, a reverse transcriptase enzyme generates a DNA molecule from a target RNA molecule.

In some embodiments, in a method or composition provided above or elsewhere herein involving a first oligonucleotide primer, the first primer is complementary to a strand of a linear double-stranded nucleic acid template.

In some embodiments, in a method or composition provided above or elsewhere herein involving a second oligonucleotide primer, the second primer is complementary to a strand of a linear double-stranded nucleic acid template.

In some embodiments, in a method or composition provided above or elsewhere herein involving a first oligonucleotide primer and a second oligonucleotide primer wherein both the first oligonucleotide primer and the second oligonucleotide primer are complementary to a complementary strand of the linear double-stranded nucleic acid template, the first oligonucleotide primer and the second oligonucleotide primer are complementary to different strands of the linear double-stranded nucleic acid template.

In some embodiments, in a method or composition provided above or elsewhere herein involving a first oligonucleotide primer and a second oligonucleotide primer and at least one adaptor, at least one of the first oligonucleotide primer and the second oligonucleotide primer is complementary to the adaptor.

In some embodiments, in a method or composition provided above or elsewhere herein involving a primer, the primer is an oligodeoxyribonucleotide.

In some embodiments, in a method or composition provided above or elsewhere herein involving at least a first adaptor and a second adaptor, the first and second adaptors contain the same nucleotide sequence. In some embodiments, in a method or composition provided above or elsewhere herein involving at least a first adaptor and a second adaptor, the first and second adaptors contain different nucleotide sequences.

In some embodiments, in a method or composition provided above or elsewhere herein involving at least a first adaptor and a second adaptor, the first and second adaptors contain a single strand component of a restriction enzyme recognition sequence for different restriction enzymes. In some embodiments, in a method or composition provided above or elsewhere herein involving at least a first adaptor and a second adaptor, the first and second adaptors contain a single strand component of a restriction enzyme recognition sequence for the same restriction enzyme.

In some embodiments, in a method or composition provided above or elsewhere herein involving an adaptor, the adaptor has a nucleotide sequence such that under certain conditions it forms a stem-loop structure containing a blunt end at the combined 5' and 3' termini of the adaptor.

In some embodiments, in a method or composition provided above or elsewhere herein involving an adaptor, the adaptor has a nucleotide sequence such that under certain conditions it forms a stem-loop structure containing a sticky end at the combined 5' and 3' termini of the adaptor. In some embodiments, adaptor which forms a stem-loop structure containing a sticky end at the combined 5' and 3' termini of the adaptor has a 3' overhang in the stem region. In some embodiments, adaptor which forms a stem-loop structure containing a sticky end at the combined 5' and 3' termini of the adaptor has a 5' overhang in the stem region.

In some embodiments, in a method or composition provided above or elsewhere herein involving an adaptor, the adaptor has a nucleotide sequence such that under certain conditions it forms a stem-loop structure containing a half of a full double-stranded restriction enzyme recognition sequence at the combined 5' and 3' termini of the adaptor.

In some embodiments, in a method or composition provided above or elsewhere herein involving an adaptor, the adaptor contains a nucleotide sequence comprising a 5' region, a middle region, and a 3' region, wherein the 5' region and 3' region of the sequence are complementary to each other such that under certain conditions they anneal to each other and form the stem of a stem-loop structure, and the stem comprises an outermost part comprising the 5' and 3' terminal nucleotides and an inner part.

In some embodiments, in a method or composition provided above or elsewhere herein involving an adaptor containing a stem comprising an outermost part and an inner part, the outermost part of the adaptor contains a blunt end. In some embodiments, in a method or composition provided above or elsewhere herein involving an adaptor containing a stem comprising an outermost part and an inner part, the outermost part of the adaptor contains a sticky end. In some embodiments, in a method or composition provided above or elsewhere herein involving an adaptor containing a stem comprising an outermost part and an inner part, the outermost part of the adaptor contains half of a full double-stranded restriction enzyme recognition sequence. In some embodiments, in a method or composition provided above or elsewhere herein involving an adaptor containing a stem comprising an outermost part and an inner part wherein the outermost part of the adaptor contains half of a full double-stranded restriction enzyme recognition sequence, if two of the adaptors are ligated end-to-end (i.e. at the outermost part of the adaptor), the complete version of the full double-stranded restriction enzyme recognition sequence is formed from the combination of the two halves of the full double-stranded restriction enzyme recognition sequence provided by the two adaptors. In some embodiments, in a method or composition provided above or elsewhere herein involving an adaptor comprising a stem comprising an outermost part and an inner part, the inner part comprises a full double-stranded restriction enzyme sequence.

In some embodiments, in a method or composition provided above or elsewhere herein involving a linear double-stranded nucleic acid template comprising a first complementary strand and a second complementary strand, the first complementary strand and second complementary strand contain the same number of nucleotides. In some embodiments, in a method or composition provided above or elsewhere herein involving a linear double-stranded nucleic acid template comprising a first complementary strand and a second complementary strand, the first complementary strand and second complementary strand contain a different number of nucleotides. In some embodiments, in a method or composition provided above or elsewhere herein involving a linear double-stranded nucleic acid template, the template has blunt ends on both ends. In some embodiments, in a method or composition provided above or elsewhere herein involving a linear double-stranded nucleic acid template, the template has sticky ends on both ends.

In some embodiments, in a method or composition provided above or elsewhere herein involving a polymerase, the polymerase has strand-displacement activity. In some embodiments, in a method or composition provided above or elsewhere herein involving a polymerase which generates the extension product of a first primer, the polymerase has strand-displacement activity. In some embodiments, in a method or composition provided above or elsewhere herein involving a polymerase which generates the extension product of a second primer, the polymerase has strand-displacement activity. In some embodiments, in a method or composition provided above or elsewhere herein involving a polymerase, the polymerase is a DNA polymerase.

In some embodiments, in a method or composition provided above or elsewhere herein involving ligation of two or more nucleic acids, the ligation is performed enzymatically. In some embodiments, in a method or composition provided above or elsewhere herein involving ligation of two or more nucleic acids, the ligation is performed chemically.

In some embodiments, in a method or composition provided above or elsewhere herein involving treating a linear double-stranded nucleic acid template comprising two complementary strands with two adaptor molecules under conditions such that a circular strand comprising the two adaptor molecules and the two complementary strands is formed, the conditions comprise contacting the adaptor molecules and the linear double-stranded nucleic acid template with a ligase.

In some embodiments, in a method provided above or elsewhere herein involving a circular strand comprising two complementary strands of a linear double-stranded nucleic acid template, the method may comprise a step to promote or maintain the separation of the two complementary strands within the circular strand (e.g. to minimize self-annealing of the sequences of the two complementary strands within the circular strand). In some embodiments, the step may include heating the circular strand. In some embodiments, the step may include incubating the circular strand with a molecule which interferes with the annealing of the sequence of the complementary strands. In some embodiments, a molecule which interferes with the annealing of the sequences of the complementary strands may be a primer which is complementary to one the complementary strands. In some embodiments, the primer may contain one or more alternative nucleotides (e.g. a locked nucleic acid nucleotide).

In some embodiments, all steps of a method provided herein may be performed at a temperature of no greater than 90, 85, 80, 75, 70, 65, 60, 55, 50, 45, 40, 35, 30, 25, 20, 15, or 10 C.

In some embodiments, two or more steps of a method provided herein are performed simultaneously.

In some embodiments, in a method provided above or elsewhere herein involving amplification of a linear double-stranded nucleic acid template, the linear double-stranded nucleic acid template is amplified at least 2, 5, 10, 20, 50, 100, 1000, 10,000, or 100,000-fold within 1, 2, 3, 5, 10, 15, 20, 30, 40, 50, 60, 90, or 120 minutes of initiation of the method.

In some embodiments, the initiation point of a method provided above or elsewhere herein involving amplification of a linear double-stranded nucleic acid template is the point at which all reagents for performing the method have been combined in a single vessel.

In some embodiments, a method provided herein comprises treating one or more of the reaction components with a nucleic acid dye. In some embodiments, a method provided herein comprises measuring a fluorescent signal from an assay comprising the method.

In some embodiments, a vessel or kit provided herein comprises a nucleic acid dye.

BRIEF DESCRIPTION OF THE DRAWINGS

In the drawings,

FIG. 1 is a general schematic of a method provided herein.

Figure 2:
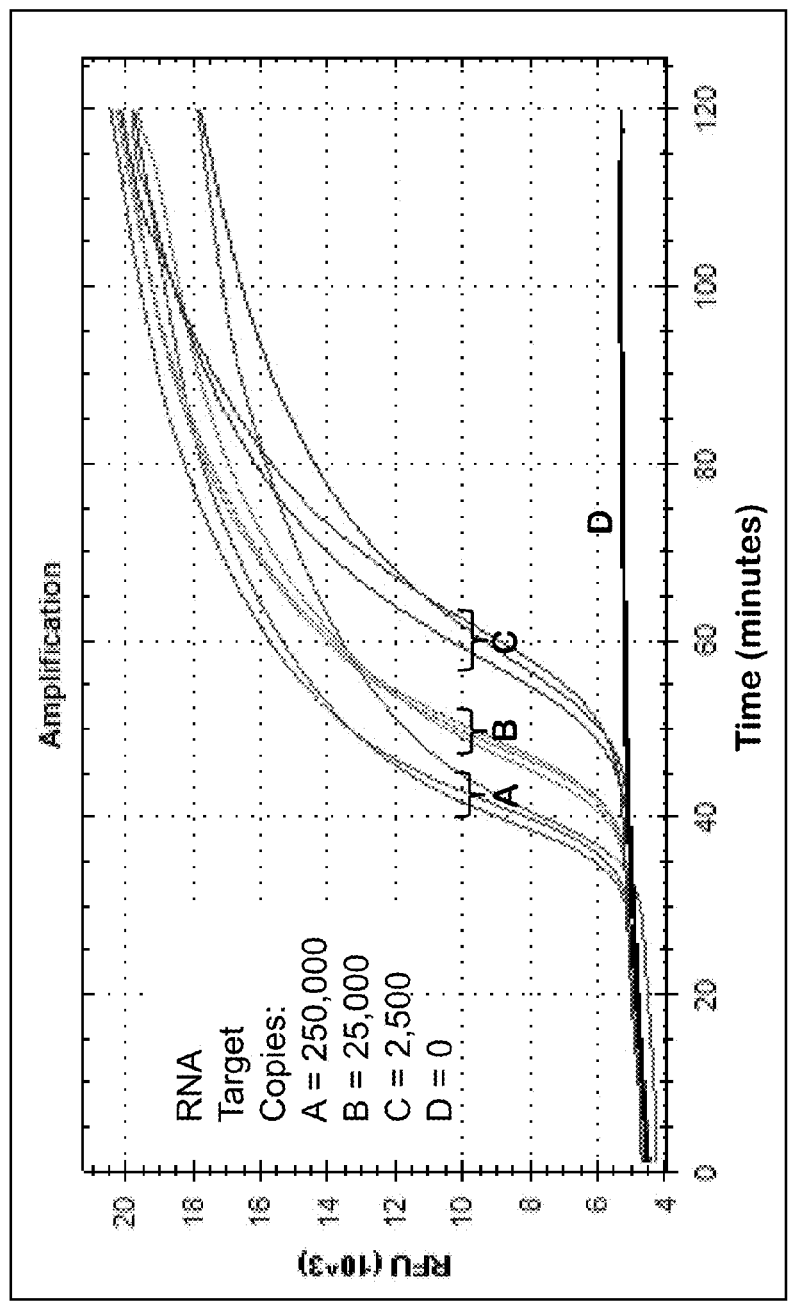
FIG. 2 is a graph depicting results from reactions performed according to a method provided herein.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

Provided herein are methods and compositions relating to the amplification of nucleic acids.

Definitions

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded.

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

As used herein, a "linear double-stranded nucleic acid" refers to a double-stranded nucleic acid having two open ends (e.g. a "first end" and a "second end"). "Linear double-stranded nucleic acids" thus differ from circular double-stranded nucleic acids, which do not have any open ends. A "linear double-stranded nucleic acid" comprises two complementary nucleic acid strands. A "linear double-stranded nucleic acid" may have any conformation (e.g. bent, twisted, straight, etc.), provided it has two open ends. At each end of a linear double-stranded nucleic acid, the 5' terminus of one strand and the 3' terminus of the other strand of the linear double-stranded nucleic acid are present. As used herein, a "linear double-stranded nucleic acid template" refers to a linear double-stranded nucleic acid that may be amplified according to a method provided herein.

As used herein, a "target" nucleic acid or molecule refers to a nucleic acid of interest. A target nucleic acid/molecule may be of any type, including single-stranded or double stranded DNA or RNA (e.g. mRNA). In some instances, a target nucleic acid may be a nucleic acid which may directly function as a linear double-stranded nucleic acid template in a method provided herein (e.g. a linear double-stranded DNA molecule), or it may be a nucleic acid which requires further processing or conversion to function as a linear double-stranded nucleic acid template in a method provided herein (e.g. mRNA).

As used herein, "complementary" sequences refer to two nucleotide sequences which, when aligned anti-parallel to each other, contain multiple individual nucleotide bases which pair with each other. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide.

As used herein, "adaptor type" refers to an adaptor molecule having a particular nucleotide sequence. If two adaptors have any difference in nucleotide sequence or chemical modification, they are considered to be of two different "types".

As used herein, a "single-strand component of a restriction enzyme recognition sequence" refers to a nucleotide sequence which is the same as the sequence of one strand of a restriction enzyme recognition sequence, read in the 5' to 3' direction. For example, a "single-strand component of a restriction enzyme recognition sequence" for the restriction enzyme EcoRI is "GAATTC", for the restriction enzyme StuI is "AGGCCT", and for the restriction enzyme BsmI is "GAATGCN" or "NGCATTC".

As used herein, a "full double-stranded restriction enzyme recognition sequence" refers to the double-stranded structure formed when both strands of a restriction enzyme recognition sequence (e.g. a "single-strand component of a restriction enzyme recognition sequence" and its complement) are annealed to each other.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a linear double-stranded nucleic acid template, such that a concatemer may contain two or more copies of a linear double-stranded nucleic acid template.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

As used herein, in the context of two or more polymeric molecules (e.g. nucleic acids, proteins), "corresponds to", "corresponding to", and the like refers to polymeric molecules or portions thereof which have the same or similar sequence of component elements (e.g. nucleotides, amino acids). For example, if a first nucleic acid is described as containing a region which "corresponds to" the sequence of a second nucleic acid, the relevant region of the first nucleic acid has a nucleotide sequence which is the same or similar to the sequence of the second nucleic acid.

Methods

In some embodiments, methods for amplifying a linear double-stranded nucleic acid template are provided.

In some embodiments, a method for amplifying a linear double-stranded nucleic acid template may include one or more of the following general steps:

(1) Generating a circular strand from a linear double-stranded nucleic acid template, wherein the circular strand contains the single-strand component of at least one restriction enzyme recognition sequence;

(2) Treating the circular strand from step (1) with a first oligonucleotide primer and a polymerase, under conditions such that an extension product of the first primer is synthesized;

(3) Treating the extension product of the first primer from step (2) with a second oligonucleotide primer and a polymerase, under conditions such that an extension product of the second primer is synthesized which is complementary to the extension product of the first primer of step (2), to produce a new double-stranded nucleic acid comprising at least a portion of the extension product of the first primer and at least a portion of the extension product of the second primer;

(4) Treating the new double-stranded nucleic acid from step (3) with a restriction enzyme that recognizes a full double-stranded restriction enzyme recognition sequence corresponding to the single-strand component of a restriction enzyme recognition sequence of step (1), under conditions such that the new double-stranded nucleic acid from step (3) is cleaved to form two or more shorter double-stranded nucleic acids which comprise at least a portion of a copy of the linear double-stranded nucleic acid template of step (1).

In some embodiments, methods provided herein may further include repeating steps (1)-(4) for one, two, three or more additional cycles, using a shorter double-stranded nucleic acid of step (4) as the linear double-stranded nucleic acid template in step (1).

In some embodiments, methods provided herein may include, prior to step (1), generating a linear double-stranded nucleic acid template for use in step (1) from a single-strand target molecule. A single-strand target molecule may be DNA or RNA (e.g. mRNA).

In some embodiments, methods provided herein may include any of the features, steps, or components discussed elsewhere herein. In addition, although in some embodiments nucleic acid amplification methods provided herein are described as containing four steps, it should be understood that amplification methods provided herein may be described as containing any number of steps (e.g. 2, 3, 4, 5, 6, 7, 8, 9, 10, or more). In some embodiments, two, three, or more aspects of amplification methods provided herein provided herein may be performed simultaneously. It should also be understood that while methods provided herein have been described herein using a limited number of terms, phrases, and steps for purposes of brevity, methods provided herein could also be described using other terms, phrases and steps which are not provided herein but which also accurately describe methods provided herein.

Additional information about various general steps of certain methods provided herein is provided below.

(1) Generating a Circular Strand from a Linear Double-Stranded Nucleic Acid Template, Wherein the Circular Strand Contains the Single-Strand Component of at Least One Restriction Enzyme Recognition Sequence In some methods provided herein, a linear double-stranded nucleic acid template ("template") comprising two complementary strands may be converted into a circular single nucleic acid strand ("circular strand"). A linear double-stranded nucleic acid template has a first end and a second end, and the two complementary strands may be referred to as a "first strand"/"first complementary strand" and a "second strand"/"second complementary strand". Typically, each end of a template comprises the 5' terminus of one strand (e.g. the first strand), and the 3' terminus of the other strand (e.g. the second strand).

Any linear double-stranded nucleic acid of interest may be used as a template. The template may have blunt ends at both the first end and the second end, it may have sticky ends at both the first end and the second end, or it may have a blunt end at one end and a sticky end at the other end. The double stranded nucleic acid template may be obtained or generated by any method for obtaining or generating a linear double stranded nucleic acid, such as by cleavage of a larger molecule or by synthesis from a precursor single-stranded molecule.

To convert a linear double-stranded nucleic acid template into a circular strand, the template is treated such that the first and second complementary strands of the template become directly or indirectly linked end-to-end as part of the same circular single nucleic acid chain. For example, to generate a circular strand from the template, the 3' terminus of the first strand may be directly or indirectly linked to the 5' terminus of the second strand, and the 3' terminus of the second strand may be directly or indirectly linked to the 5' terminus of the first strand. Thus, in embodiments, both the first and second complementary strands of the template become part of the same circular strand.

During the generation of a circular strand from a linear double-stranded nucleic acid template, the termini of the first and second complementary strands of the template may be directly linked or indirectly linked to form the circular strand. Termini may be indirectly linked, for example, through an adaptor molecule which bridges the 3' terminus of a first strand and the 5' terminus of a second strand. Strands may be directly linked, for example, through the direct linkage of the 3' terminus of a first strand with the 5' terminus of a second strand. Termini of strands may be directly linked, for example, when a plurality of nucleotides at the end of one or both strands are not paired with each other, such that the 5' terminus of one strand or the 3' terminus of the other strand is free to move to a position adjacent to the terminus of the other strand, where linkage of the termini may occur.

In some embodiments, in a circular strand, the 3' terminus of the first strand is indirectly linked to the 5' terminus of the second strand, and the 3' terminus of the second strand is indirectly linked to the 5' terminus of the first strand. In other embodiments, in a circular strand, the 3' terminus of the first strand is directly linked to the 5' terminus of the second strand, and the 3' terminus of the second strand is directly linked to the 5' terminus of the first strand. In other embodiments, in a circular strand, the 3' terminus of the first strand is indirectly linked to the 5' terminus of the second strand, and the 3' terminus of the second strand is directly linked to the 5' terminus of the first strand. In other embodiments, in a circular strand, the 3' terminus of the first strand is directly linked to the 5' terminus of the second strand, and the 3' terminus of the second strand is indirectly linked to the 5' terminus of the first strand.

In some embodiments, to generate a circular strand from a linear double stranded nucleic acid template, at each of the first end and the second end of the template, the termini of the first and second strands may be connected to each other via one or more adaptor molecules ("adaptors"). Thus, in some embodiments, within a circular strand, the sequence of one complementary strand of the linear double-stranded nucleic acid template may be separated sequentially from the sequence of the other complementary strand at each terminus by the sequence of at least one adaptor molecule.

Any adaptor described elsewhere herein may connect the first and second strands of the template. For example, an adaptor may contain a single nucleic acid strand having a 5' terminus and a 3' terminus. Adaptors of the same type or of different types may connect the first and second strands of the template. For example, an adaptor of type "A" may connect the termini of the first and second strands at the first end of the template, and an adaptor of type "A" may also connect the termini of the first and second strands at the second end of the template. In another example, an adaptor of type "A" may connect the termini of the first and second strands at the first end of the template, and an adaptor of type "B" may connect the termini of the first and second strands at the second end of the template. In some embodiments, two, three, four, five, or more adaptor types are incorporated into a circular strand during the generation of a circular strand from a template. In some embodiments, two, three, four, five, or more adaptor types are present in a reaction for the generation of a circular strand from a template, but are not all necessarily incorporated into a circular strand.

Any number of adaptors may connect the termini of the first and second complementary strands at each end of the template (e.g. 1, 2, 3, 4, 5, or more adaptors). For example, one adaptor may connect the termini of the first and second strands at the first end of the template, and one adaptor may connect the termini of the first and second strands at the second end of the template. In another example, two adaptors may connect the termini of the first and second strands at the first end of the template (i.e. there are two adaptors between the termini of the first and second strands), and two adaptors may connect the termini of the first and second strands at the second end of the template. In another example, one adaptor may connect the termini of the first and second strands at the first end of the template, and two adaptors may connect the termini of the first and second strands at the second end of the template. In some embodiments, the same number of adaptors may connect the termini of the first and second strands at both of the first end and the second end of the template. In some embodiments, a different number of adaptors may connect the termini of the first and second strands at each of the first end and the second end of the template.

The various components of the circular strand (e.g. the first and second strands of the template, adaptors) may be sequentially connected covalently or non-covalently in the strand. Components of the circular strand may be linked covalently, for example, through their phosphate backbones. Components of the circular strand may be linked non-covalently, for example, through ionic ligand-receptor bonds.

In some embodiments, components of the circular strand are linked together through ligation. Ligation may involve the formation of a phosphodiester bond between the 5' phosphate of one nucleotide and the 3' hydroxyl of another nucleotide. Ligation may be mediated by an enzyme having nucleotide ligase activity, such as a DNA ligase. Any suitable ligase may be used to ligate together components of the circular strand. Alternatively, ligation may not be mediated by an enzyme, and instead, may involve a chemical reaction with reactive groups—e.g. phosphorothioate. Methods for chemical ligation are disclosed, for example, in U.S. Pat. Nos. 5,859,232 and 5,151,510, which are herein incorporated by reference in their entirety.

In a circular strand containing the two strands of the template and one, two, three, four or more adaptors, the termini of the strands of the template may be directly linked to the adaptors. In an alternative, one or more additional nucleotides (e.g. 1, 2, 3, 4, 5, 6, 7, 8, 9, 10, 15, 20, or more) may be present in the circular strand between at least one of the adaptors and at least one of the template strands. In an alternative, in the circular strand, one or more nucleotides (e.g. 1, 2, 3, 4, 5, 6, 7, 8, 9, 10, 15, 20 or more) may be absent from the terminus of an adaptor or a template strand at the location of the adaptor-template strand linkage (e.g. if during the formation of the circular strand, a small number of nucleotides are lost from the terminus of a template strand or an adaptor when the template strand and adaptor are linked).

In some embodiments, in a reaction to generate a circular strand containing adaptors and a linear double-stranded nucleic acid template, one or more primers (a "bridging primer") may be provided which are capable of annealing to a portion (typically a region including the terminus) of both an adaptor and a first or second complementary strand of the template. In some circumstances, a bridging primer may anneal to a portion of an adaptor and then to a portion of a complementary strand (or vice versa), thereby bringing the adaptor and the template into close proximity and supporting subsequent ligation of the adaptor to termini of the first and second strands at one end of the template, and the formation of the circular strand. In some circumstances, at least two different bridging primers may be provided, wherein each bridging primer is capable of annealing to a portion of a strand at a different end of the template, thereby supporting bringing adaptors into close proximity with both ends of the template. In some circumstances, a bridging primer may function as a first oligonucleotide primer (described further below) of an amplification method provided herein. In some circumstances, a bridging primer does not support the generation of an extension product (e.g. if the primer lacks a 3' hydroxyl group).

A circular strand may contain the single-strand component of a restriction enzyme recognition sequence. The single-strand component of a restriction enzyme sequence may be located anywhere within the circular strand. In some embodiments, the single-strand component of a restriction enzyme sequence is located in the circular strand in a region corresponding to the first or second strand of the template. In some embodiments, the single-strand component of a restriction enzyme sequence is located in the circular strand in a region not corresponding to the first or second strand of the template. In some embodiments, the single-strand component of a restriction enzyme sequence is located in the circular strand in a region corresponding to an adaptor.

In some embodiments, in a circular strand containing a single-strand component of a restriction enzyme sequence, there is not also a complementary sequence to the single-strand component of a restriction enzyme sequence. In such circumstances, the single-strand component of a restriction enzyme sequence cannot pair with another sequence in the circular strand to form a localized full double-stranded restriction enzyme recognition sequence. In some embodiments, in a circular strand containing a single-strand component of a restriction enzyme sequence, there is a complementary sequence to the single-strand component of a restriction enzyme sequence. In such circumstances, the single-strand component of a restriction enzyme sequence may pair with another sequence in the circular strand to form a localized full double-stranded restriction enzyme recognition sequence.

One or more single-strand components of a restriction enzyme recognition sequence may be present in a circular strand. In some embodiments, one, two, three, four, five, or more single-strand components of a restriction enzyme recognition sequence may be present in a circular strand. In some embodiments, within a circular strand, a single-strand component of a restriction enzyme recognition sequence is present sequentially both before and after a region of the strand corresponding to the first complementary strand of the template, such that the first and second complementary strands are separated at both termini by a single-strand component of a restriction enzyme recognition sequence. In some embodiments, within the circular strand, a single-strand component of a restriction enzyme recognition sequence is present sequentially after the region of the strand corresponding to the first complementary strand and after the region of the strand corresponding second complementary strand, such that the first and second complementary sequences are separated at both termini by a single-strand component of a restriction enzyme recognition sequence.

In a circular strand containing two or more single-strand components of a restriction enzyme recognition sequence, the single-strand components of a restriction enzyme recognition sequence may be for the same restriction enzyme, or for different restriction enzymes. The circular strand may contain the single-strand component of any restriction enzyme recognition sequence. Restriction enzyme recognition sequences are well known in the art, and are described, for example in Molecular Cloning: A Laboratory Manual, M. R. Green and J. Sambrook, Cold Spring Harbor Laboratory Press (2012), which is herein incorporated by reference in its entirety.

(2) Treating the Circular Strand from Step (1) with a First Oligonucleotide Primer and a Polymerase, Under Conditions Such that an Extension Product of the First Primer is Synthesized;

The circular strand may be treated with an oligonucleotide primer and a polymerase under conditions such that an extension product of the primer is synthesized. The oligonucleotide primer may be referred to as the "first oligonucleotide primer" or "first primer". The extension product of the first primer may be referred to as the "first primer extension product".

The first primer may be of any primer type described elsewhere herein. For example, the primer may contain standard deoxyribonucleotides, standard ribonucleotides, non-standard nucleotides, or a combination thereof.

The first primer may be complementary to and anneal to any location on the circular strand. In some embodiments, the first primer may be complementary to a sequence in the circular strand corresponding to the first or the second complementary strand of the template. In some embodiments, the first primer may be complementary to a sequence in the circular strand corresponding to an adaptor. In some embodiments, the first primer may be complementary to a sequence in the circular strand corresponding to a portion of the first or the second complementary strand and a portion of an adaptor.

In some circumstances, in a method described herein, it may be advantageous to use a first primer which is complementary to a sequence in a circular strand corresponding to the first or the second complementary strand of the template, rather than to use a first primer which is complementary to a sequence in the circular strand corresponding to an adaptor. A first primer with binding specificity for the first or the second complementary strand will support selective amplification of circular strands which contain regions corresponding to the first or the second complementary strand of the template. In contrast, if the first primer is complementary to a sequence in the circular strand which exclusively corresponds to, for example, an adaptor sequence, the first primer may support the amplification of non-specific products which contain the sequence of the adaptor but not the sequence of the first or second complementary strand of the template. Thus, in some embodiments, lower background amplification or a greater amount of template-specific amplification may occur in a method provided herein when a first primer which is complementary to a sequence of the first or the second complementary strand is used to generate an extension product of the first primer (as compared to using a first primer which is complementary to an adaptor).

However, primers and adapters may be designed which reduce or eliminate any potential problems due to amplification of non-specific elements. For example, adapters may be designed in ways described elsewhere herein to minimize the formation of non-specific adaptor-adaptor ligation products.

In some circumstances, in a method described herein, it may be advantageous to use a first primer which is complementary to a sequence in a circular strand corresponding to an adaptor, rather than to use a first primer which is complementary to a sequence in the circular strand corresponding to the first or the second complementary strand of the template. A first primer with binding specificity for the adaptor may be advantageous in circumstances where, for example, the sequence of the template is not known or when multiple different amplification reactions are being performed with the same adaptor. In such circumstances, use of a first primer with binding specificity for the adaptor may facilitate the performance of the reaction(s), by eliminating or reducing need for template-specific primers.

A first primer extension product may be generated with a polymerase. The polymerase may be of any type described elsewhere herein. In some embodiments, the polymerase may have strand displacement activity. Polymerases having strand displacement activity include phi29 DNA polymerase, Klenow Fragment of DNA Polymerase I, Vent$_R$ DNA polymerase, Deep Vent$_R$ DNA polymerase, 9° N$_m$ DNA polymerase, and Large Fragment of Bst DNA Polymerase.

The polymerase may catalyze the formation of a first primer extension product. Typically, the extension product is generated from the 3' end of the first primer. During the generation of the first primer extension product, the first primer may be covalently linked to the synthesized extension product, such that the first primer becomes part of the molecule described herein as the "first primer extension product". The generated first primer extension product is complementary to the sequence of the circular strand.

Synthesis of a first primer extension product with a polymerase having strand displacement activity may result in the generation of an extension product having more nucleotides (i.e. a greater length) than the circular strand. If the polymerase synthesizes an extension product starting from the 3' end of the first primer and continues to synthesize an extension product around the length of the circular strand, it may eventually encounter the 5' end of the first primer. At that point, the polymerase may continue to move and synthesize extension product along the circular strand, thereby sequentially displacing the first primer and portions of the earlier-generated first primer extension product. The polymerase may continue for multiple rounds of circling and synthesis of an extension product along the length of the circular strand, thereby generating an extension product that may contain multiple copies of a sequence which is complementary to the sequence of the circular strand. Thus, for example, the first primer extension product may contain at least 1, 2, 3, 4, 5, 6, 7, 8, 9, 10, 12, 15, 20, 30, 40, 50, 60, 70, 80, 90, or 100 copies of a sequence which is complementary to the sequence of the circular strand.

A first primer extension product containing multiple copies of a sequence which is complementary to the circular strand may be a concatemer. The process of generating a first primer extension product from the circular strand which may contain multiple copies of a sequence which is complementary to the sequence of the circular strand may be referred to herein as "rolling circle amplification".

Appropriate conditions for the generation of a first primer extension product may include any condition sufficient to support polymerase-based nucleic acid synthesis. Example conditions for polymerase-based nucleic acid synthesis are known in the art and are provided, for example, in Green and Sambrook, supra. Non-limiting components for a polymerase-based nucleic acid synthesis reaction may include one or more of: polymerase enzyme (at a concentration between, for example, 0.01 and 10 units enzyme per 50 microliters reaction volume, or any range therein including, for example, between 0.01-1, 0.1-10, 0.1-5, 0.5-10, 0.5-5, 0.5-2, 1-10, or 1-5 units enzyme per 50 microliters reaction volume, where 1 unit of enzyme will incorporate 15 nmol of dNTPs into polymerization product in 30 minutes at 75 C.); template (at a concentration of at least, for example, 1, 10, 100, 1,000, 10,000, or 100,000 copies per reaction); primer (at a concentration between, for example, 0.01 and 10 micromolar, or any range therein including, for example, between 0.01-1, 0.1-10, 0.1-5, 0.5-5, or 0.5-2 micromolar); dNTPs (e.g. dATP, dTTP, dGTP, and dCTP, at a concentration between, for example, 50 and 500 micromolar each of dATP, dTTP, dGTP, and dCTP, or any range therein including, for example, between 50-350, 100-500, 100-300, 200-500, or 300-400 micromolar each of dATP, dTTP, dGTP, and dCTP); salt (e.g. KCl or potassium acetate, at a concentration between, for example, 1 and 200 millimolar, or any range therein including, for example, between 1-100, 1-50, 1-20, 1-10, 10-20, 10-50, or 10-200 millimolar); buffer (e.g. Tris-HCl or Tris-acetate, pH 7.8-8.5, at a concentration between, for example, 1 and 100 millimolar, or any range therein including, for example, between 1-50, 1-20, 1-10, 1-5, 10-100, 20-100, or 50-100 millimolar); and magnesium ions (at a concentration between, for example 0.1 and 10 millimolar, or any range therein, including, for example, between 0.1-5, 0.1-1, 0.5-10, 0.5-5, or 0.5-2.5 millimolar). Additional non-limiting components for a polymerase-based nucleic acid synthesis reaction may increase the speed of the reaction, increase the fidelity of the reaction, or increase the stability of enzymes or DNA in the reaction, and may include one or more of: gelatin (at a concentration between, for example, 0.0001% and 0.1% w/v), BSA (at a concentration between, for example, 0.01 and 1 microgram per microliter), sucrose (at a concentration between, for example 0.01 molar and 0.8 molar), trehalose (at a concentration between, for example 0.01 molar and 0.8 molar), DMSO (at a concentration between, for example, 0.01 and 10% v/v), betaine (at a concentration between, for example, 0.1 and 10 molar), formamide (at a concentration between, for example, 0.1 and 10% v/v), glycerol (at a concentration between, for example, 0.1 and 20% v/v), polyethylene glycol (at a concentration between, for example, 0.1 and 20% v/v), non-ionic detergents [e.g. NP-40 (at a concentration between, for example, 0.01 and 1% v/v), Tween-20 (at a concentration between, for example, 0.01 and 1% v/v), and Triton X-100 (at a concentration between, for example, 0.01 and 1% v/v)], ammonium ions [e.g. ammonium sulfate (at a concentration between, for example, 1 and 100 millimolar)], and EDTA (at a concentration between, for example, 0.001 and 0.1 millimolar). Other reagents may also be present in a polymerase-based nucleic acid synthesis reaction provided herein. For example, reagents to sufficient to synthesize RNA reaction products or reaction products containing non-standard nucleotides may be used. Conditions sufficient to support polymerase-based nucleic acid synthesis may include a variety of temperatures and pH values. For example, the pH of a of a polymerase-based nucleic acid synthesis reaction be between, for example pH 6.0 and pH 10.0, such as 6.5, 7, 7.5, 7.8, 7.9, 8, 8.1, 8.2, 8.5, 9, or 9.5. The temperature of a polymerase-based nucleic acid synthesis reaction may be constant or varied. A constant temperature may be between, for example, 10 C. and 95 C., such as 20, 25, 30, 35, 37, 40, 42, 45, 50, 55, 60, 65, 70, 75, 80, or 85 C. A varied temperature may at two or more different temperatures between, for example 10 C. and 95 C., such two or more temperatures selected from 20, 25, 30, 35, 37, 40, 42, 45, 50, 55, 60, 65, 70, 75, 80, or 85 C.

(3) Treating the Extension Product of the First Primer from Step (2) with a Second Oligonucleotide Primer and a Polymerase, Under Conditions Such that an Extension Product of the Second Primer is Synthesized which is Complementary to the Extension Product of the First Primer of Step (2), to Produce a New Double-Stranded Nucleic Acid Comprising at Least a Portion of the Extension Product of the First Primer and at Least a Portion of the Extension Product of the Second Primer;

The first primer extension product may be treated with an oligonucleotide primer and a polymerase under conditions such that an extension product of the primer is synthesized. The oligonucleotide primer may be referred to as the "second oligonucleotide primer" or "second primer." The extension product of the second primer may be referred to as the "second primer extension product".

The second primer may be of any type described elsewhere herein. For example, the primer may contain standard deoxyribonucleotides, standard ribonucleotides, non-standard nucleotides, or a combination thereof.

The second primer may be complementary to and anneal to any location on the first primer extension product. In some embodiments, the second primer may anneal to a sequence in the first primer extension product corresponding to the first or the second complementary strand of the template. In some embodiments, the second primer may anneal to a sequence in the first primer extension product corresponding to a sequence complementary to an adaptor (i.e. the sequence of the second primer may correspond to a sequence in an adaptor). In some embodiments, the second primer may be complementary to a sequence in the first primer extension product corresponding to a portion of the first or the second complementary strand and a portion of a sequence complementary to an adaptor.

In some circumstances, in a method described herein, it may be advantageous to use a second primer which is complementary to a sequence in the first primer extension product corresponding to the first or the second complementary strand of the template, rather than to use a second primer which is complementary to a sequence in the first primer extension product corresponding to a sequence complementary to an adaptor. A second primer with binding specificity for the first or the second complementary strand will support selective amplification of a first primer extension product which contains regions corresponding to the first or the second complementary strand. In contrast, if the second primer is complementary to a sequence in the first primer extension product which exclusively corresponds to, for example, a sequence complementary to an adaptor sequence, the second primer may support the amplification of non-specific products which contain the sequence of the adaptor but not the sequence of the first or second complementary strand. Thus, in some embodiments, lower background amplification or a greater amount of template-specific amplification may occur in a method provided herein when a second primer which is complementary to a sequence of the first or the second complementary strand is used to generate an extension product of the second primer (as compared to using a second primer which is complementary to a sequence complementary an adaptor).

In some circumstances, in a method described herein, it may be advantageous to use a second primer which is complementary to a sequence in a first primer extension product corresponding to a sequence complementary to the adaptor, rather than to use a second primer which is complementary to a sequence in the first primer extension product corresponding to the first or the second strand of the template. A second primer with binding specificity for a sequence complementary to the adaptor may be advantageous in circumstances where, for example, the sequence of the template is not known or when multiple different amplification reactions are being performed with the same adaptor. In such circumstances, use of a second primer with binding specificity for a sequence complementary to the adaptor may facilitate the performance of the reaction(s), by eliminating or reducing a need for template-specific primers.

In some embodiments, in a method described herein, the first primer may be complementary to a sequence in the first or the second complementary strand of the template, and the second primer may be complementary to a sequence in the first or the second complementary strand of the template. In other embodiments, the first primer may be complementary to a sequence in an adaptor molecule, and the second primer may be complementary to a sequence complementary to a sequence in an adaptor molecule. In other embodiments, the first primer may be complementary to a sequence complementary to a sequence in an adaptor molecule, and the second primer may be complementary to a sequence in the first or the second complementary strand of the template. In other embodiments, the first primer may be complementary to a sequence in the first or the second complementary strand of the template, and the second primer may be complementary to a sequence complementary to a sequence in an adaptor molecule.

A second primer extension product may be generated with a polymerase. The polymerase may be of any type described elsewhere herein. In some embodiments, the polymerase may have strand displacement activity. In some embodiments, the polymerase may be of the same type as used for the generation of the first primer extension product. In some embodiments, the polymerase may be of a different type as used for the generation of the first primer extension product.

The polymerase may catalyze the formation of a second primer extension product. Typically, the extension product is generated from the 3' end of the second primer. During the generation of the second primer extension product, the second primer may be covalently linked to the synthesized extension product, such that the second primer becomes part of the molecule described herein as the "second primer extension product". The second primer extension product is complementary to at least a portion of the sequence of the first primer extension product. The second primer extension product may contain one or more copies of the sequence of the circular strand.

Appropriate conditions for the generation of a second primer extension product may include any condition sufficient to support polymerase-based nucleic acid synthesis, and may include any conditions discussed elsewhere herein for polymerase-based nucleic acid synthesis. In some embodiments, conditions for the generation of a second primer extension product are the same as the conditions for the generation of a first primer extension product. In some embodiments, conditions for the generation of a second primer extension product are different from the conditions for the generation of a first primer extension product.

Synthesis of a second primer extension product may result in the generation of a new double-stranded nucleic acid containing at least a portion of the first primer extension product and at least a portion of the second primer extension product ("new double-stranded nucleic acid"). The new double-stranded nucleic acid may contain at least a portion of the first primer extension product and the entire second primer extension product. The new double-stranded nucleic acid may contain, for example, 1, 2, 3, 4, 5, 6, 7, 8, 9, 10, 12, 15, 20, 30, 40, 50, 60, 70, 80, 90, 100, 200, 300, 400, 500, or more copies of the linear double-stranded nucleic acid template. In some embodiments, the new double-stranded nucleic acid may contain regions between some or each of the copies of the linear double-stranded nucleic acid template. In some embodiments, the regions between the copies of the linear double-stranded nucleic acid template may contain full double-stranded restriction enzyme recognition sequences corresponding to the single-strand component of a restriction enzyme recognition sequence present in the circular strand.

In some embodiments, within the new double-stranded nucleic acid, some or each of the copies of the double-stranded nucleic acid template may be separated by regions containing the nucleotide sequence of adaptors used during the generation of the circular strand to connect the termini of the first and second complementary strands of the template, and by nucleotide sequences complementary to the adaptors. In some embodiments, these regions containing the nucleotide sequence of adaptors may contain a full double-stranded restriction enzyme recognition sequence corresponding to the single-strand component of a restriction enzyme recognition sequence present in the corresponding adaptor molecule (4) Treating the New Double-Stranded Nucleic Acid from Step (3) with a Restriction Enzyme that Recognizes a Full Double-Stranded Restriction Enzyme Recognition Sequence Corresponding to the Single-Strand Component of a Restriction Enzyme Recognition Sequence of Step (1), Under Conditions Such that the New Double-Stranded Nucleic Acid from Step (3) is Cleaved to Form Two or More Shorter Double-Stranded Nucleic Acids which Comprise at Least a Portion of a Copy of the Linear Double-Stranded Nucleic Acid Template of Step (1).

The new double-stranded nucleic acid may contain one or more copies of the full double-stranded restriction enzyme recognition sequence corresponding to the single-strand component of the restriction enzyme recognition sequence present in the circular strand. In some embodiments, regions of the new double-stranded nucleic acid which contain copies of the full double-stranded restriction enzyme recognition sequence are part of regions of the new double-stranded nucleic acid which correspond to an adaptor. This configuration may occur, for example, when the single-strand component of a restriction enzyme recognition sequence in the circular strand was originally in an adaptor that became part of the circular strand.

The new double-stranded nucleic acid may be treated with a restriction enzyme that recognizes and cleaves the full double-stranded restriction enzyme recognition sequence in the new double-stranded nucleic acid. Typically, the restriction enzyme will not be able to recognize or cleave a nucleic acid containing only a single strand component of a restriction enzyme recognition sequence. Instead, the restriction enzyme will generally only recognize and cleave a nucleic acid containing the corresponding full double-stranded restriction enzyme recognition sequence. Accordingly, in some embodiments, a restriction enzyme will not recognize or cleave the single strand component of a restriction enzyme recognition sequence present in a circular strand or adaptor, but will recognize and cleave the corresponding full double-stranded restriction enzyme recognition sequence present in a new double-stranded nucleic acid.

Treating the new double-stranded nucleic acid with a restriction enzyme that recognizes the restriction enzyme recognition sequence present in the circular strand may result in the cleavage of the new double-stranded nucleic acid by the restriction enzyme into two or more shorter new double-stranded nucleic acids ("shorter double-stranded nucleic acids"). One or more of the shorter double-stranded nucleic acids may contain one or more copies of the linear double-stranded nucleic acid template. In addition, one or more of the shorter double-stranded nucleic acids may contain a double-stranded version of an adaptor sequence (i.e. an adaptor sequence annealed to a nucleic acid having a sequence complementary to the adaptor sequence), or portion thereof. In some embodiments, one or more shorter double-stranded nucleic acids may contain a copy of the linear double-stranded nucleic acid template flanked on one or both ends by a portion of a double-stranded version of an adaptor sequence. In such circumstances, one or both ends of the shorter double-stranded nucleic acid may contain a portion of the double-stranded restriction enzyme recognition sequence recognized by the restriction enzyme which cleaved the new double-stranded nucleic acid.

Multiple shorter double-stranded nucleic acids may be generated from the cleavage of a new double-stranded nucleic acid. In some embodiments, 1, 2, 3, 4, 5, 6, 7, 8, 9, 10, 15, 20, 25, 30, 35, 40, 45, 50, 60, 70, 80, 90, 100, 200, 300, 400, 500 or more shorter new double-stranded nucleic acids may be generated from a single new double-stranded nucleic acid. One or more of the shorter double-stranded nucleic acids may contain a copy of the linear double-stranded nucleic acid template. In certain embodiments, 1, 2, 3, 4, 5, 6, 7, 8, 9, 10, 15, 20, 25, 30, 35, 40, 45, 50, 60, 70, 80, 90, 100, 200, 300, 400, 500 or more shorter new double-stranded nucleic acids which contain a copy of the linear double-stranded nucleic acid template may be generated from a single new double-stranded nucleic acid.

In order to treat a new double-stranded nucleic acid with a restriction enzyme that recognizes and cleaves the full double-stranded restriction enzyme recognition sequence in the new double-stranded nucleic acid, the reaction contains a restriction enzyme which recognizes the full double-stranded restriction enzyme recognition sequence. The restriction enzyme may have a concentration, for example, between 0.01 and 10 units restriction enzyme per 50 microliters of reaction volume, or any range therein including, for example, between 0.01-5, 0.01-1, 0.1-10, 0.1-5, 0.1-1, 0.5-10, 0.5-5, 0.5-2.5, 1-10, and 1-5 units per 50 microliters reaction volume, where 1 unit of enzyme is the amount required to digest 1 micrograms of lambda phage DNA in one hour at 25 C. The conditions for treating a new double-stranded nucleic acid with a restriction enzyme that recognizes and cleaves the full double-stranded restriction enzyme recognition sequence in the new double-stranded nucleic acid may be the same or different than conditions for the generation of a second primer extension product. In some embodiments, the conditions for treating a new double-stranded nucleic acid with a restriction enzyme that recognizes and cleaves the full double-stranded restriction enzyme recognition sequence in the new double-stranded nucleic acid may include any of the conditions sufficient to support polymerase-based nucleic acid synthesis discussed elsewhere herein. In some embodiments, the restriction enzyme is also present in reactions to generate a circular strand from a template, to generate a first primer extension product, or to generate a second primer extension product.

Optionally, Repeating Steps (1)-(4) for One or More Additional Cycles, Using a Shorter Double-Stranded Nucleic Acid of Step (4) as the Linear Double-Stranded Nucleic Acid Template in Step (1).

In some embodiments, one or more shorter double-stranded nucleic acids generated from the restriction enzyme cleavage of a new double-stranded nucleic acid may be used as the linear double-stranded nucleic acid template in one or more additional cycles of a method provided herein. For example, 1, 2, 3, 4, 5, 6, 7, 8, 9, 10, 15, 20, 25, 30, 35, 40, 45, 50, 60, 70, 80, 90, 100, 200, 300, 400, 500 or more shorter double-stranded nucleic acids may be generated from the restriction enzyme cleavage of a new double-stranded nucleic acid, and 1, 2, 3, 4, 5, 6, 7, 8, 9, 10, 15, 20, 25, 30, 35, 40, 45, 50, 60, 70, 80, 90, 100, 200, 300, 400, 500 or more of these shorter double-stranded nucleic acids may be used as the linear double-stranded nucleic acid template in another cycle of a method provided herein. In some embodiments, only shorter double-stranded nucleic acids which contain a copy of the original linear double-stranded nucleic acid template (or portion thereof) may be used the linear double-stranded nucleic acid template in another cycle of a method provided herein. For example, if one or both of the first primer or second primer are complementary to a sequence in the first or second strand of the template, only shorter double-stranded nucleic acids which contain a copy of the original linear double-stranded nucleic acid template (or relevant portion thereof) will be amplified in a subsequent round of a method provided herein. In some embodiments, only shorter double-stranded nucleic acids which contain a copy of the adaptor (or portion thereof) may be used the linear double-stranded nucleic acid template in another cycle of a method provided herein. For example, if one or both of the first primer or second primer are complementary to a sequence in the adaptor, only shorter double-stranded nucleic acids which contain a copy of the original adaptor (or relevant portion thereof) will be amplified in a subsequent round of a method provided herein.

In some embodiments, one or more steps of a method provided herein may be performed for multiple cycles. For example, according to a method provided herein, a shorter double-stranded nucleic acid may be generated from an original linear double-stranded nucleic acid template. The shorter double-stranded nucleic acid may then be used as the linear double-stranded nucleic acid template in a subsequent round of a cycle provided herein. This process may repeat itself 1, 2, 3, 4, 5, 6, 7, 8, 9, 10, 15, 20, 25, 30, 35, 40, 45, 50, 60, 70, 80, 90, 100, 200, 300, 400, 500 or more times, each time leading to an increase in the number copies of the original linear double-stranded nucleic acid template. In some embodiments, in a method provided an original linear double-stranded nucleic acid template may be amplified exponentially, such that with each cycle, the number of copies of the original linear double-stranded nucleic acid template at least doubles.

FIG. 1 provides a schematic of an example of an amplification method provided herein. The various elements depicted in this and other figures provided herein are examples only; any of the variations relating to the different elements and steps of methods described herein may be used. Additionally, the elements of this and other figures are not necessarily to scale and are not limiting regarding the shapes of the molecules.

A linear double-stranded nucleic acid template 110 may be provided (FIG. 1A). The template 110 may contain a first complementary strand 111 and a second complementary strand 112. The linear double-stranded nucleic acid template 110 has a first end 110a and a second end 110b. The first end 110a may contain the 5' terminus of the first strand 111 and the 3' terminus of the second strand 112. The second end 110b may contain the 3' terminus of the first strand 111 and the 5' terminus of the second strand 112.

Two adaptors 121, 131 ("Adaptor A" and "Adaptor B", respectively) may be provided with the linear double-stranded nucleic acid template 110. Each adaptor may comprise a single nucleic acid strand, and may contain a 5' terminus and a 3' terminus. Adaptor A 121 and Adaptor B 131 may each contain the single strand component of a restriction enzyme recognition sequence. Adaptor A 121 and Adaptor B 131 may have the same or different nucleic acid sequences.

A ligase may be provided with the two or more adaptors 121, 131 and the linear double-stranded nucleic acid template 110. The ligase may catalyze the covalent linking of the 3' terminus of the first adaptor 121 to the 5' terminus of the first strand 111 and the 5' terminus of the first adaptor 121 to the 3' terminus of the second strand 112. The ligase may also catalyze the covalent linking of the 5' terminus of the second adaptor 131 to the 3' terminus of the first strand 111 and the 3' terminus of the second adaptor 131 to the 5' terminus of the second strand 112. Covalent linkage of the first strand 111 and the second strand 112 to each other through an adaptor molecule 121, 131 at each of the first end 110a and the second end 110b of the linear double-stranded nucleic acid template 110 may result in generation of a circular strand 140 (FIG. 1B). The circular strand may contain the nucleotides of the first strand 111 and the second strand 112, separated sequentially within the circular strand by the nucleotides of the first adaptor 121 and the nucleotides of the second adaptor 131.

A first primer 151 may be incubated with and anneal to the circular strand 140 (FIG. 1C). The first primer 151 may be complementary to any region of the circular strand 140. A nucleic acid polymerase 154 may be incubated with the first primer 151 and the circular strand 140. The polymerase 154 may synthesize an extension product of the first primer 150 (FIG. 1D), which may include the first primer. The polymerase 154 may have strand displacement activity. The first primer extension product 150 may be complementary to the circular strand 140. As part of the first primer extension product 150, sequences which are complementary to various components of the circular strand are generated [e.g. a sequence 112 which is complementary to the first strand 111 is generated (it has the same sequence as the second strand 112); a sequence 111 which is complementary to the second strand 112 is generated (it has the same sequence as the first strand 111); a sequence 122 which is complementary to the first adaptor 121 is generated; and a sequence 132 which is complementary to the second adaptor 131 is generated]. The polymerase 154 may have strand displacement activity, such that when the polymerase encounters the 5' end of the first primer extension product 150 annealed to the circular strand 140, it displaces the 5' end of the first primer extension product and subsequent regions, and continues to synthesize extension product of the first primer (FIG. 1E). As a result of the strand displacement activity of the polymerase 154, the synthesized first primer extension product 150 may ultimately contain more nucleotides and have a greater length than the circular strand 140.

A second primer 161 may be incubated with and anneal to the first primer extension product 150 (FIG. 1F). The second primer 161 may be complementary to any region of the first primer extension product 150. A nucleic acid polymerase 154 may be incubated with the second primer 161 and the first primer extension product 150. The polymerase may synthesize an extension product of the second primer 160, which may include the second primer (FIG. 1G). The second primer extension product 160 may be complementary to the first primer extension product 150. The synthesis of the second primer extension product 160 may result in the generation of a new double-stranded nucleic acid 170, containing at least a portion of the second primer extension product 160 and at least a portion of the first primer extension product 150. The new double-stranded nucleic acid 170 may contain one or more copies of the original linear double-stranded nucleic acid template 110 (first strand 111 annealed to second strand 112). The new double-stranded nucleic acid 170 may also contain one or more copies of Adaptor A 121 and Adaptor B 131, and the complements thereof (Adaptor A 121 annealed to the complement thereof 122, and Adaptor B 131 annealed to the complement thereof 132; both also annotated with diagonal slashes). Within the regions of the new double-stranded nucleic acid 170 corresponding to Adaptor A 121 and the complement thereof 122 and Adaptor B 131 and the complement thereof 132, one or more copies of the full double-stranded restriction enzyme recognition sequence corresponding to the single-strand component of the restriction enzyme recognition sequence present in each of these adaptors may be present. The full double-stranded restriction enzyme recognition sequence present in the combination of Adaptor A 121 and the complement thereof 122 is marked by a vertical line 125. The full double-stranded restriction enzyme recognition sequence present in the combination of Adaptor B 131 and the complement thereof 132 is also marked by a vertical line 135.

The new double-stranded nucleic acid 170 may be incubated with a restriction enzyme which recognizes the full double-stranded restriction enzyme recognition sequence corresponding to the single strand component of a restriction enzyme recognition sequence present in one or both of Adaptor A and Adaptor B (FIG. 1G). The restriction enzyme may cleave the new double-stranded nucleic acid 170 at or near the site(s) of the full double-stranded restriction enzyme recognition sequence 125, 135. These sites 125, 135 may be within the regions of the new double-stranded nucleic acid 170 corresponding to Adaptor A 121 and the complement thereof 122 and Adaptor B 131 and the complement thereof 132.

Cleavage of the new double-stranded nucleic acid 170 at the one or more full double-stranded restriction enzyme recognition sequences 125, 135 may result in the generation of two or more shorter double-stranded nucleic acids 181, 182 (FIG. 1G). The shorter double-stranded nucleic acids 181, 182 may contain a copy of the original linear double-stranded nucleic acid template 110 (111+112). The copy of the original linear double-stranded nucleic acid template 110 (111+112) in the shorter double-stranded nucleic acids 181, 182 may be flanked on both sides by sequences corresponding to a portion of Adaptor A 121 and the complement thereof 122 or Adaptor B 131 and the complement thereof 132.

One or more shorter double-stranded nucleic acids 181, 182 may then be used as a linear double-stranded nucleic acid template in a new cycle of the method outlined in FIG. 1. For example, the steps of FIGS. 1A-1G may be repeated, using a shorter double stranded nucleic acid 181 or 182 as the linear double-stranded nucleic acid template in FIG. 1A of the next cycle. Multiple cycles of this process may be repeated, thereby leading to the generation of many copies of the original linear double-stranded nucleic acid template 110. In some embodiments, some or all of the many copies of the original linear double-stranded nucleic acid template 110 may be flanked one or both sides by additional nucleotides, such as one or more sequences corresponding to one or more portions of Adaptor A 121 and the complement thereof 122 or Adaptor B 131 and the complement thereof 132

Methods provided herein may be performed at a variety of temperatures. In some embodiments, all steps of a method are performed at the same temperature. Thus, temperature cycling such as in PCR is not necessary with methods disclosed herein. In some embodiments, methods provided herein may be performed at two or more different temperatures. In some embodiments, a reaction mixture containing reagents for a method provided herein is incubated at two or more different temperatures. In some examples, different temperatures may be selected to optimize the rate, accuracy, or other feature of different steps of a method provided herein. For example, different temperatures may be selected to increase the enzymatic activity of a ligase, a polymerase, or a restriction enzyme. In some examples, different temperatures may be selected to increase the binding specificity of a primer to a template or to increase the accessibility of a template to a primer (e.g. higher temperatures may promote the separation of duplex template nucleic acids). In some embodiments, all of the steps of a method provided herein are performed at a temperature of no greater than 80, 70, 60, 50, 40, 30, 20 or 10° C. In some embodiments, a method provided herein is performed at a temperature between 20-60, 30-70, 40-80, 30-40, 35-45, 40-50, 45-55, 50-60, or 55-65° C. Methods disclosed herein may be performed with or without a thermocycler.

As one consideration, the temperature used for a step of a method provided herein may be selected to be appropriate for the enzyme(s) being used in the step of the method. In some embodiments, for methods in which a ligase, polymerase, and restriction enzyme are present in the same vessel, the temperature(s) of the reaction is selected such that it does not significantly impair the activity of any of the enzymes (e.g. the temperature of the reaction may be selected such that each enzyme in the reaction has a half-life of at least 24, 12, 6, 4, 3, 2, 1, 0.75, 0.5, 0.25, or 0.1 hours). Alternatively, methods may be performed at a temperature that impairs the activity of one or more of the enzymes (e.g. the temperature of the reaction may be selected such that at least one of the enzymes in the reaction has a half-life of no more than 24, 12, 6, 4, 3, 2, 1, 0.75, 0.5, 0.25, or 0.1 hours). In some embodiments, if a method is performed at a temperature or other condition (e.g. pH) that impairs the activity of one or more the enzymes, additional enzyme may be added to the reaction at one or more intervals after the initiation of the method to supplement the activity of the impaired enzyme(s).

In some embodiments, for at least some steps of a method provided herein, the step or method is performed at a temperature below the melting temperature (Tm) of the first or second primer. Generally, melting temperature is regarding as the temperature at which 50% of nucleic acids having a given mutually complementary nucleotide sequence are base-paired.

In some embodiments, one or more steps of a method provided herein occur in the same reaction vessel (e.g. tube, tip, container, etc.). In some embodiments, all of the steps of a method occur in the same reaction vessel.

Reagents for methods provided herein can all be provided together at the start of a reaction, or they may be added sequentially, where after one, two, or more steps new reagents are added to a reaction. In some circumstances, new reagents (e.g. enzymes, primers, adaptors) may be added to a reaction vessel during the course of the reaction, to increase the amount of reagents available to act on substrates or to replace the function of reagents that have become inactivated (e.g. enzymes). New reagents may be added to a reaction at one or more selected time intervals after the initiation of a reaction of a method provided herein (for example, at 1, 3, 5, 7, 10, 15, 20, 30, 45, or 60 minutes after the initiation of a reaction).

In some embodiments, one or more steps of a method provided herein may occur simultaneously. For example, during a method provided herein, the second primer may anneal to the first primer extension product and serve as a template for the synthesis of the second primer extension product while the first primer extension product continues to be synthesized along the circular strand (i.e. synthesis of the second primer extension product may start before the synthesis of the first primer extension product is complete). In another example, once multiple shorter double-stranded nucleic acids are generated in a method provided herein, two or more of the shorter double-stranded nucleic acids may simultaneously be used as a linear double-stranded nucleic acid template in a new cycle of the method. In another example, a circular strand generated during a first cycle of a method provided herein may be used as a circular strand during a second cycle of the method, such that during the second cycle of the method, two circular strands are available (the two circular strands are: i) the circular strand generated during the first cycle and ii) the circular strand generated during the second cycle). Other reaction steps provided herein may also occur simultaneously.

In some embodiments, two or more sets of first and second primers are provided in a method provided herein, where each set contains a first primer and a second primer, and where different primer sets are complementary to different linear double-stranded nucleic acid templates. Inclusion of two or more primer sets in a method provided herein may support the simultaneous amplification of multiple different linear double-stranded nucleic acid templates in the same reaction vessel. This may be useful, for example, for amplifying multiple templates of interest in a sample, or for assaying for the presence of multiple different templates in a sample. In some embodiments, 1, 2, 3, 4, 5, 6, 7, 8, 9, 10, 15, 20, 25, 30, 40, 50, 60, 70, 100, 200, 500 or more sets of first and second primers are provided in a method provided herein, in order to amplify or assay for the presence of 1, 2, 3, 4, 5, 6, 7, 8, 9, 10, 15, 20, 25, 30, 40, 50, 60, 70, 100, 200, 500 or more different linear double-stranded nucleic acid templates.

In some embodiments, in a method provided herein, a linear double-stranded nucleic acid template may be amplified rapidly. For example, in some embodiments, a linear double-stranded nucleic acid template may be amplified at least 500-fold within 0.1, 0.5, 1, 3, 5, 10, 15, 20, 30, 40, 50, 60, 90, 120, or 180 minutes of starting the method. In another example, in some embodiments, a linear double-stranded nucleic acid template may be amplified at least 10,000-fold within 0.1, 0.5, 1, 3, 5, 10, 15, 20, 30, 40, 50, 60, 90, 120, or 180 minutes of starting the method. In another example, in some embodiments, a linear double-stranded nucleic acid template may be amplified at least 5, 10, 25, 50, 100, 250, 500, 1,000, 5,000, 10,000, 50,000, 100,000, 500,000, or 1,000,000-fold over the original amount of the linear double-stranded nucleic acid template present in a reaction mixture at the start of the method within 0.1 minute, 0.5 minute, 1 minute, 3 minutes, 5 minutes, 10 minutes, 15 minutes, 20 minutes, 30 minutes, 40 minutes, 50 minutes, 60 minutes, 90 minutes, 2 hours, 3 hours, 4 hours, 6 hours, 8 hours, 12 hours, 16 hours, or 24 hours of initiation of the method. In some embodiments, when a method is initiated, all of the reagents for the first step of the method are in a vessel containing the reaction mixture for the method. In some embodiments, when a method is initiated, all of the reagents for all of the steps of the method are in a vessel containing the reaction mixture for the method.

In some embodiments, in a method provided herein, a linear double-stranded nucleic acid template may be amplified at greater than a linear rate. In some embodiments, in a method provided herein, a linear double-stranded nucleic acid template may be amplified exponentially. In some embodiments, in a method provided herein, a linear double-stranded nucleic acid template may at least double in number with each cycle of the method. In some embodiments, in a method provided herein, a linear double-stranded nucleic acid template may at least double in number every 1, 2, 3, 5, 10, 15, 20, 25, 30, 45, 60, 90, 120, 180, or 240 minutes after the initiation of the method. In some embodiments, a linear double-stranded nucleic acid template may amplified at least 5, 10, 25, 50, 100, 250, 500, 1,000, 5,000, 10,000, 50,000, 100,000, 500,000, 1,000,000, or 10,000,000-fold over the original amount of the linear double-stranded nucleic acid template present in the reaction at the start of the method.

With methods provided herein, a linear double-stranded nucleic acid template may be amplified by multiple mechanisms. For example, multiple copies of a linear double-stranded nucleic acid template may be generated as part of shorter double stranded nucleic acids in a single cycle of a method provided herein. In another example, when a method provided herein is repeated for multiple cycles, multiple circular strands containing a copy of the linear double-stranded nucleic acid template may be available (e.g. a circular strand generated in a particular cycle, plus circular strands that were generated in previous cycles may all be available). Then, from the multiple circular strands, multiple shorter double stranded nucleic acids may be generated.

In some embodiments, in reaction mixtures provided herein for the performance of amplification methods provided herein, multiple steps are of an amplification method provided herein are simultaneously performed. For example, in some embodiments, in a single reaction mixture, two or more of the following are occurring simultaneously: generation of a circular strand from a linear double-stranded nucleic acid template, generation of a first primer extension product, generation of a second primer extension product and generation of a new double-stranded nucleic acid, and cleavage of a new double-stranded nucleic acid into two or more shorter double-stranded nucleic acids. In some embodiments, each of the above is occurring simultaneously in a reaction mixture provided herein.

In some embodiments, separate to or concurrent with any step of a method provided herein, a condition or reaction component may be provided to promote or maintain the separation of the sequences of the two complementary strands of the linear double-stranded nucleic acid template within the circular strand. Such conditions or reaction components may facilitate the annealing of the first primer to the circular strand and thereby accelerate a method provided herein. For example, the circular strand may be subjected to a temperature that that promotes the "breathing" (i.e. brief periods of localized rupture of hydrogen bonds connecting base pairs) or continuous separation of the sequences of the two complementary strands of the template within the circular strand. In another example, the circular strand may be subjected to a molecule which interferes with the annealing of the complementary strands of the template within the circular strand. Such a molecule may be, for example, a primer which has a nucleotide sequence that is complementary to a complementary strand of the template. In the case of a primer which binds specifically to a complementary strand of the template, the primer may contain one or more non-standard nucleotides [e.g. locked nucleic acids (described in, for example, Vester B and Wengel J, *Biochemistry*, 43(42), Oct. 26, 2004, pp. 13233-41, which is herein incorporated by reference in its entirety)]. A primer which can bind specifically to a complementary strand in a circular strand and interfere with the annealing of the sequences of the complementary strands within the circular strand may be referred to herein as an "invasion primer". In some circumstances, an invasion primer may be configured such that it does not support the addition of nucleotides at its 3' end by a polymerase (e.g. it may lack a 3' OH group).

Detection of Reactions

Progress of a method provided herein may be monitored in multiple different ways. In one embodiment, a reaction may be assayed for a nucleic acid amplification product (e.g. for the level of the product or the rate of its generation). In another embodiment, a reaction may be assayed for the activity of a polymerase along a nucleic acid template (e.g. for movement of a polymerase along an adaptor, the circular strand or the first primer extension product). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In some embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bis-benzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions [or example, where increased turbidity is correlated with formation of reaction products and reaction by-products (e.g. pyrophosphate complexed with magnesium)].

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or processes associated with the generation of nucleic acids may be used with methods and compositions provided herein.

In some embodiments, a nucleic acid probe which contains a nucleotide sequence complementary to a portion of a complementary strand of the template, circular strand or first primer extension product and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus. The probe may further have a nucleotide sequence containing, in order, at least a first, second, and third region, where the first and third regions are complementary to each other, and where at least a portion of the second region is complementary to a portion of a complementary strand of a template, circular strand or first primer extension product (the probe "detection sequence"). In some embodiments, the length of the second region may be greater than the length of the first or third regions. In some embodiments, the length of the second region may be between 10 and 40 nucleotides, and the length of first and third regions may be between 4 and 10 nucleotides. The probe may have at least two different conformations: (A) a conformation where the probe is not annealed to its detection sequence and where the first and third regions are annealed to each other; this conformation may be a "stem-loop" structure, where the first and third regions form the stem and the second region forms the loop, and (B) a conformation where the probe is annealed to its detection sequence; in this conformation, the second region or a portion thereof is annealed to its detection sequence and the first and third regions are not annealed to each other. In conformation (A) of the probe, the fluorescent reporter and quencher (which are located at opposite termini of the probe/at the outer ends of the first and third regions) may be in close proximity to each other (both being at the end of the stem structure formed by the annealing of the first and third regions), such that the fluorescent reporter is quenched. In conformation (B) of the probe, the fluorescent reporter and quencher may not be in close proximity to each other, such that the fluorescent reporter is not quenched. The probe may be used to monitor accumulation of a selected reaction product, for example, under reaction conditions where the probe may either form a stem-loop structure or anneal to its detection sequence. In some embodiments, if the detection sequence is present, the probe may anneal to the detection sequence, and the probe may fluoresce in response to light of a wavelength of the fluorphore's excitation spectrum. In contrast, if the detection sequence is not present, the probe may form a stem-loop structure, and not fluoresce in response to light of a wavelength of the fluorphore's excitation spectrum.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched. The probe may be used to monitor accumulation of a selected reaction product, for example, under reaction conditions where the probe may either anneal to the primer or anneal to its detection sequence. In some embodiments, if the detection sequence is present, the probe may anneal to the detection sequence, and the probe may fluoresce in response to light of a wavelength of the fluorphore's excitation spectrum. In contrast, if the detection sequence is not present, the probe may remain paired with the primer, and not fluoresce in response to light of a wavelength of the fluorphore's excitation spectrum.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorphores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be monitored or performed in a device or module therein as disclosed in U.S. patent application Ser. No. 13/769,779, filed Feb. 18, 2013, which is herein incorporated by reference in its entirety.

Using methods provided herein, specific amplification products of a linear double-stranded nucleic acid template of interest may be identified within, for example, 30 seconds, 1 minute, 3 minutes, 5 minutes, 10 minutes, 15 minutes, 20 minutes, 30 minutes, 45 minutes, 60 minutes, 90 minutes, 120 minutes, 180 minutes, or 240 minutes of initiation of an amplification reaction. In other examples, using methods provided herein, amplification reactions which are positive for a linear double-stranded nucleic acid template of interest may be identified when as few as 10, 50, 100, 500, 1000, 5000, 10,000, 50,000, 100,000, 500,000, or 1,000,000 copies of the template are generated. In other examples, using methods provided herein, the presence of a linear double-stranded nucleic acid template of interest in a sample containing as few as 1, 2, 3, 4, 5, 10, 15, 20, 25, 30, 40, 50, 100, 200, 500, 1000, 5000, or 10,000 copies of the template of interest may be identified.

Methods provided herein may be performed for any length of time. Typically, the method will be performed for a length of time sufficient to monitor, for example, the rate of nucleic acid replication, the occurrence of polymerase activity, or the accumulation of amplification product. In some embodiments, a method provided herein may be performed for a total of less than 10 seconds, 30 seconds, 1 minute, 5 minutes, 10 minutes, 20 minutes, 30 minutes, 45 minutes, 1 hour, 2 hours, 3 hours, 4 hours, 6 hours, 8 hours, 12 hours, 16 hours, or 24 hours, by which time the rate of nucleic acid replication, the occurrence of polymerase activity, or the accumulation of amplification product was measured.

Methods provided herein may be terminated in various ways. In one embodiment, steps of a method may end upon the reduction in concentration or complete consumption of one or more reagents involved in one or more steps of the method (e.g. dNTPs). In another embodiment, steps of a method may end upon inactivation of one or more enzymes involved in one or more steps of the method (e.g. polymerases). Enzymes may be inactivated by various ways. For example, enzymes may gradually lose enzymatic activity over time due to random events that affect the structure of the enzyme, or enzymes may be exposed to a condition to accelerate the inactivation of the enzyme activity (e.g. high heat, extreme pH, etc.).

In some embodiments, methods provided herein may include preparing a reaction mixture containing reagents for performing an amplification method provided herein. For example, methods provided herein may include preparing a reaction mixture containing any one or more of: a linear double-stranded nucleic acid template, a first primer, a second primer, one or more adaptors, a ligase, a polymerase, and a restriction enzyme. In some embodiments, methods provided herein may include preparing a reaction mixture containing each of: a linear double-stranded nucleic acid template, a first primer, a second primer, an adaptor, a ligase, a polymerase, and a restriction enzyme. In some embodiments, methods provided herein may further comprise including a reverse transcriptase in the reaction mixture. The linear double-stranded nucleic acid template, first primer, second primer, adaptors, ligase, polymerase, restriction enzyme, and reverse transcriptase may have any of the features described elsewhere herein. Methods provided herein may further comprise including any other reagents described elsewhere herein useful for performing an amplification method provided herein in the reaction mixture (e.g. dNTPs, buffer, salts, water, BSA, etc.). In some embodiments, reaction mixtures may be prepared a vessel. In some embodiments, methods provided herein may further comprise incubating a reaction mixture for a period of time after all of the reagents for an amplification method provided herein are added to the reaction mixture. A reaction mixture may be incubated for example, for no more than 0.1, 0.5, 1, 2, 3, 5, 10, 15, 20, 25, 30, 40, 50, 60, 70, 80, 90, 120, 150, 180, 240, or 480 minutes after the combination of the all of the reagents for an amplification method provided herein in a reaction vessel. The reaction mixture may be incubated one or more selected temperatures. The temperature may be any temperature for performing an amplification method described elsewhere herein. In some embodiments, a reaction mixture may be measured for assay results after no more than 0.1, 0.5, 1, 2, 3, 5, 10, 15, 20, 25, 30, 40, 50, 60, 70, 80, 90, 120, 150, 180, 240, or 480 minutes after the combination of the all of the reagents for an amplification method provided herein in a reaction vessel.

Linear Double-Stranded Nucleic Acid Template

Various linear double-stranded nucleic acid templates may be used with compositions and methods provided herein.

The linear double-stranded nucleic acid template may contain DNA, RNA, or a mixture thereof. The linear double-stranded nucleic acid template may contain two separate complementary strands (a "first strand"/"first complementary strand" and a "second strand"/"second complementary strand").

The linear double-stranded nucleic acid template may be of any size. For example, the linear double-stranded nucleic acid template may be at least 2, 3, 4, 5, 6, 7, 8, 9, 10, 12, 14, 16, 18, 20, 25, 30, 35, 40, 45, 50, 60, 70, 80, 90, 100, 150, 200, 250, 300, 350, 400, 500, 750, 1000, or 1500 nucleotide base pairs in length. In another example, the double-stranded nucleic acid template may be between 2 and 100,000, between 5 and 100,000, between 10 and 100,000, between 15 and 100,000, between 20 and 100,000, between 25 and 100,000, between 30 and 100,000, between 50 and 100,000, between 70 and 100,000, between 100 and 100,000, between 200 and 100,000, between 2 and 10,000, between 5 and 10,000, between 10 and 10,000, between 15 and 10,000, between 20 and 10,000, between 25 and 10,000, between 30 and 10,000, between 50 and 10,000, between 70 and 10,000, between 100 and 10,000, between 200 and 10,000, between 2 and 5,000, between 5 and 5,000, between 10 and 5,000, between 15 and 5,000, between 20 and 5,000, between 25 and 5,000, between 30 and 5,000, between 50 and 5,000, between 70 and 5,000, between 100 and 5,000, between 200 and 5,000, between 2 and 3,000, between 5 and 3,000, between 10 and 3,000, between 15 and 3,000, between 20 and 3,000, between 25 and 3,000, between 30 and 3,000, between 50 and 3,000, between 70 and 3,000, between 100 and 3,000, between 200 and 3,000, between 2 and 1,000, between 5 and 1,000, between 10 and 1,000, between 15 and 1,000, between 20 and 1,000, between 25 and 1,000, between 30 and 1,000, between 50 and 1,000, between 70 and 1,000, between 100 and 1,000, between 200 and 1,000, between 2 and 500, between 5 and 500, between 10 and 500, between 15 and 500, between 20 and 500, between 25 and 500, between 30 and 500, between 50 and 500, between 70 and 500, between 100 and 500, or between 200 and 500 nucleotide base pairs in length.

A linear double-stranded nucleic acid template may have blunt ends at both the first end and the second end of the template, it may have sticky ends at both the first end and the second end of the template, or it may have a blunt end at one end of the template and a sticky end at the other end of the template. The two separate complementary strands of the linear double-stranded nucleic acid template may be of the same length as each other (resulting in a linear double-stranded nucleic acid template with blunt ends), or they may be different (resulting in a linear double-stranded nucleic acid template with at least one sticky end).

The linear double-stranded nucleic acid template may have been derived from a larger double-stranded nucleic acid parent molecule (e.g. by cleavage of the larger double-stranded nucleic acid parent molecule), or it may not have been derived from a larger double-stranded nucleic acid parent molecule.

In some embodiments, the linear double-stranded nucleic acid template is a double-stranded DNA molecule that was generated from an RNA molecule (e.g. a single stranded RNA molecule, such as mRNA). A double-stranded DNA molecule may be generated from an RNA molecule through techniques that are well-known in the art, for example, through reverse transcription. Example conditions for generating a double-stranded DNA molecule from an RNA molecule are provided, for example, in RNA: A Laboratory Manual, D. Rio et al., Cold Spring Harbor Laboratory Press (2011), which is herein incorporated by reference in its entirety. Briefly, in some examples, a primer which is complementary to an mRNA sequence of interest may be incubated with: reverse transcriptase enzyme (e.g. AMV reverse transcriptase, M-MLV reverse transcriptase, Superscript II™ reverse transcriptase, Superscript III™ reverse transcriptase, or ThermoScript™ reverse transcriptase), dNTPs, and the mRNA sequence of interest. The primer may anneal to the mRNA, and then, starting from the 3' end of the primer, the reverse transcriptase may synthesize a strand of DNA complementary to the mRNA (cDNA). In some embodiments, the mRNA annealed to the cDNA may be degraded (e.g. with an RNase; the RNase may be the reverse transcriptase, which may also have RNase activity), and the cDNA may then be incubated with: a different primer which is complementary to the strand of cDNA, dNTPs, and a DNA polymerase (e.g. any DNA polymerase discussed elsewhere herein). Then, starting from the 3' end of the different primer, the DNA polymerase may synthesize a strand of DNA complementary to cDNA, thereby generating a linear double-stranded DNA molecule.

In some embodiments, a linear double-stranded DNA template may be generated from a single-stranded RNA molecule in the same reaction mixture in which the linear double-stranded DNA template is amplified according to a method provided herein. In some embodiments, the same primer may be used for both A) generation of a cDNA strand from an RNA molecule, and B) as a first or second primer in an amplification method provided herein.

Adaptors

In some embodiments, provided herein are nucleic acid adaptor molecules ("adaptors"). An adaptor may contain a single nucleic acid strand. Adaptors may be used to connect a first complementary strand and a second complementary strand of a linear double-stranded nucleic acid template, in order to generate a circular strand. Adaptors may contain DNA, RNA, or a mixture thereof, and may contain standard or non-standard nucleotides. An adaptor may contain a 5' phosphate group and a 3' hydroxyl group.

Adaptors may be of any length of nucleotides. In some embodiments, an adaptor may contain at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, at least 50, at least 60, at least 70, at least 80, at least 90, at least 100, at least 125, at least 150, at least 175, at least 200, at least 250, at least 300, at least 400, or at least 500 nucleotides. In some embodiments, an adaptor may contain 500 or fewer, 400 or fewer, 300 or fewer, 250 or fewer, 200 or fewer, 175 or fewer, 150 or fewer, 125 or fewer, 100 or fewer, 90 or fewer, 80 or fewer, 70 or fewer, 60 or fewer, 50 or fewer, 45 or fewer, 40 or fewer, 35 or fewer, 30 or fewer, 25 or fewer, 20 or fewer, 18 or fewer, 16 or fewer, 14 or fewer, 12 or fewer, 10 or fewer, 9 or fewer, 8 or fewer, 7 or fewer, 6 or fewer, 5 or fewer, 4 or fewer, or 3 or fewer nucleotides.

In some embodiments, an adaptor may contain regions which are self-complementary (i.e. the adaptor may contain internal nucleotide sequences which are capable of Watson-Crick base pairing with other nucleotide sequences in the same strand). In some embodiments, the sequences of the self-complementary regions of the adaptor are inverted relative to each other within the adaptor strand, so that the regions hybridize as anti-parallel strands. An adaptor containing self-complementary regions may, under certain conditions, form a stem-loop structure. The association and dissociation of short complementary nucleic acids occurs as an equilibrium reaction whose characteristics are determined, for example, by the temperature and salt conditions of a reaction and base content and length of the complementary sequences. The influence of these factors has been described in J. G. Wetmur ([1991] Crit. Rev. Biochem. Mol. Biol. 26; 227-259), which is incorporated by reference herein in its entirety.

In some embodiments, an adaptor containing self-complementary regions may contain self-complementary regions at or near the 5' and 3' termini of the single nucleic acid strand of the adaptor. In some embodiments, an adaptor may contain self-complementary regions at or near the 5' and 3' termini of the single nucleic acid strand such that no more than 20, 15, 10, 9, 8, 7, 6, 5, 4, 3, 2, 1, or 0 un-annealed nucleotides are present at the 5' terminus of the adaptor when the self-complementary regions of the adaptor are annealed. In some embodiments, an adaptor may contain self-complementary regions at or near the 5' and 3' termini of the single nucleic acid strand such that no more than 20, 15, 10, 9, 8, 7, 6, 5, 4, 3, 2, 1, or 0 un-annealed nucleotides are present at the 3' terminus of the adaptor when the self-complementary regions of the adaptor are annealed. In some embodiments, an adaptor may contain self-complementary regions at or near the 5' and 3' termini of the single nucleic acid strand such that no more than 20, 15, 10, 9, 8, 7, 6, 5, 4, 3, 2, 1, or 0 un-annealed nucleotides are present at either the 5' terminus or the 3' terminus of the adaptor when the self-complementary regions of the adaptor are annealed. An adaptor described herein as being configured to adopt a stem-loop structure may contain self-complementary regions at or near the 5' and 3' termini of the single nucleic acid strand of the adaptor. Such adaptors may also be described as being capable of adopting a stem-loop structure.

In some embodiments, an adaptor may contain a localized double-stranded region as a result of the annealing of self-complementary regions of the adaptor. Both strands of the localized double-stranded region of the adaptor are part of the same larger single nucleic acid strand of the adaptor.

The localized double-stranded region of the adaptor may include both the 5' and 3' terminal nucleotides of the adaptor. In some embodiments, an adaptor contains a localized double-stranded region of at least 2, 3, 4, 5, 6, 7, 8, 9, 10, 15, 20, 25, 30, 35, 40, 45, or 50 nucleotide pairs in length. In some embodiments, an adaptor contains a localized double-stranded region of at least 2, 3, 4, 5, 6, 7, 8, 9, 10, 15, 20, 25, 30, 35, 40, 45, or 50 nucleotide pairs in length, starting with annealed 5' and 3' terminal nucleotides of the adaptor. In some embodiments, an adaptor may contain 1, 2, 3, 4, 5, 6, 7, 8, 9, 10, or more separate localized double-stranded regions. A localized double-stranded region of an adaptor may be a "stem" or "stem region" of a stem-loop structure.

In some embodiments, an adaptor may contain self-complementary regions at or near the 5' and 3' termini of the single nucleic acid strand such that a stem having a blunt end is formed at the combination of the 5' and 3' termini of the single nucleic acid strand upon the annealing of self-complementary regions of the adaptor. In some embodiments, an adaptor may contain self-complementary regions at or near the 5' and 3' termini of the single nucleic acid strand such that a stem having a sticky end is formed at the combination of the 5' and 3' termini of the single nucleic acid strand upon the annealing of self-complementary regions of the adaptor. In some embodiments, an adaptor having a sticky end at the combination of the 5' and 3' termini of the single nucleic acid strand has a 3' overhang. In some embodiments, an adaptor having a sticky end at the combination of the 5' and 3' termini of the single nucleic acid strand has a 5' overhang.

In some embodiments, an adaptor containing a localized double-stranded region may contain a single-stranded loop region. The single-stranded loop region may be the "loop" of a stem-loop structure. A single-stranded loop region of an adaptor may contain 1, 2, 3, 4, 5, 6, 7, 8, 9, 10, 15, 20, 25, 30, 35, 40, 45, 50, 60, 70, 80, 90, 100, or more nucleotides. In some embodiments, an adaptor may contain 1, 2, 3, 4, 5, 6, 7, 8, 9, 10, or more separate single-stranded loop regions. A single-stranded loop region of an adaptor may contain a nucleotide sequence of interest or a percent composition of nucleotides of interest. For example, a single-stranded loop region may contain 20%, 30%, 40%, 50%, 60%, 70%, 80%, 90%, 95%, 98%, or more adenine or thymine residues in the loop region. In other examples, a single-stranded loop region may contain 3, 4, 5, 6, 7, 8, 9, 10, 12, 14, 16, 18, 20, 25, 30, 35, 40, 45, 50, or more consecutive adenine or thymine residues in the loop region. In another example, a single-stranded loop region may contain the single-strand component of a restriction enzyme recognition sequence, or a portion thereof.

In some embodiments, an adaptor may contain a stem region having a Tm of interest. A Tm of interest may be selected based on a variety of factors. In some circumstances, it may be desirable to have a Tm in the stem region such that the self-complementary regions of the adaptor stably anneal at the temperature of a reaction involving the adaptor, but also readily separate in the presence of a polymerase once the adaptor is incorporated into a circular strand. A Tm of interest for a stem region of an adaptor may be, for example, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 57, 58, 59, 60, 61, 62, 63, 64, 65, 66, 67, 68, 68, 70, 71, 72, 73, 74, or 75° C.

In some embodiments, an adaptor may contain the single-strand component of a restriction enzyme recognition sequence. The single-strand component of a restriction enzyme recognition sequence may be entirely within a single-stranded loop region of the adaptor, it may be partially within a single-stranded loop region and partially within a localized double-stranded region of the adaptor, it may be entirely within a localized double-stranded region of the adaptor, or it may be within an adaptor lacking a stem-loop structure. The presence of a single-strand component of a restriction enzyme recognition sequence in an adaptor does not preclude the presence in the same adaptor of a region which is complementary to some or all of the single-strand component of a restriction enzyme recognition sequence. In some embodiments, if an adaptor contains a single-strand component of a restriction enzyme recognition sequence and a region which is complementary to some or all of the sequence, the regions may anneal to each other under certain conditions as part of a localized double-stranded region of the adaptor.

Typically, if the single-strand component of a restriction enzyme recognition sequence does not have a complementary region within the adaptor, the single-strand component of a restriction enzyme recognition sequence in the adaptor cannot be readily recognized or cleaved by the corresponding restriction enzyme. In some embodiments, if the single-strand component of a restriction enzyme recognition sequence is entirely within a localized double-stranded region of the adaptor (i.e. if the single-strand component of a restriction enzyme recognition sequence is part of a localized full double-stranded restriction enzyme recognition sequence within the adaptor), the full double-stranded restriction enzyme recognition sequence may be situated in the adaptor such that it can be readily cleaved by the corresponding restriction enzyme. In other embodiments, if the single-strand component of a restriction enzyme recognition sequence is entirely within a localized double-stranded region of the adaptor, the full double-stranded restriction enzyme recognition sequence may be situated in the adaptor such that it cannot be readily cleaved by the corresponding restriction enzyme. For example, the full double-stranded restriction enzyme recognition sequence containing the single-strand component of a restriction enzyme recognition sequence may be immediately adjacent to a single-stranded loop region of an adaptor, and this localized structure may not support the binding of the corresponding restriction enzyme to the full double-stranded restriction enzyme recognition sequence.

The single-strand component of a restriction enzyme recognition sequence may correspond to any restriction enzyme recognition sequence. For example, the adaptor may contain a single-strand component of a restriction enzyme recognition sequence for the restriction enzyme AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FauI, Fnu4HI, FokI, FseI, FspEI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqaI, TfiI, TseI, Tsp45I, TspMI, TspRI, Tth111I, XbaI, XcmI, XhoI, XmaI, XmnI, or ZraI.

In some embodiments, an adaptor may have three general regions, in sequence (5' to 3'): A) a 5' region, B) a middle region, and C) a 3' region. The 5' and 3' regions may be complementary to each other. Under certain conditions, the 5' and 3' regions may anneal to each other, thereby forming a localized double-stranded region/stem of a stem-loop structure. The stem formed by the annealing of the 5' region and 3' region may be referred to herein as a "stem" or "terminal stem" of the adaptor. In some embodiments, the 5' and 3' regions may have any of the characteristics of self-complementary regions described elsewhere herein. The middle region may have a single-stranded conformation, and be the loop of a stem-loop structure, in which the combined 5' and 3' regions form the stem of the stem-loop structure. In some embodiments, the middle region may contain a nucleotide sequence such that under certain conditions it contains one, two, three, four, five, or more separate localized double-stranded regions and one, two, three, four, five, or more separate single-stranded regions. In some embodiments, the middle region may have any of the characteristics of a single-stranded loop region described elsewhere herein.

In some embodiments, in an adaptor having a 5' region, a middle region, and a 3' region, and where the 5' and 3' regions form a localized double-stranded region/stem of a stem-loop structure, the stem may contain at least two sub-parts: i) an "outermost part" and ii) an "inner part". The outermost part may contain the actual 5' terminal and 3' terminal nucleotides of the adaptor, plus 0, 1, 2, 3, 4, 5, 6, 7, 8, 9, or 10 additional nucleotides immediately adjacent to the 5' terminal nucleotide and 0, 1, 2, 3, 4, 5, 6, 7, 8, 9, or 10 additional nucleotides immediately adjacent to the 3' terminal nucleotide. In the outermost part of a stem, all of the nucleotides may be annealed to another nucleotide (i.e. the stem may have a blunt end), or some of the nucleotides in either the 5' or 3' region may be not annealed to another nucleotide (i.e. there may be a 5' or 3' overhang/the stem may have a sticky end). The outermost part of a stem contains an outermost base pair. The outermost base pair may include both the 5' terminal and 3' terminal nucleotides of the adaptor (in the case of a stem with a blunt end), or it may include either the 5' terminal or 3' terminal nucleotide of the adaptor plus a nucleotide no more than 10 nucleotides from the 5' or 3' terminal nucleotide of the adaptor (in the case of a stem with a sticky end). For example, if the stem has a sticky end with a 3' overhang of two nucleotides, the outermost base pair is the 5' terminal nucleotide plus the third-last nucleotide of the 3' region of the adaptor. The inner part of a stem is a part of the stem which is closer to the middle region of the adaptor than the outermost part of the stem. The inner part of a stem does not include the actual 5' or 3' terminal nucleotides of the adaptor. The inner part of the stem may start, for example, at a position 1, 2, 3, 4, 5, 6, 7, 8, 9, or 10 base pairs from the outermost base pair of the outermost part of the stem.

In some embodiments, in an adaptor containing a stem having an outermost part and an inner part, the outermost part of the stem may contain a portion of a full double-stranded restriction enzyme recognition sequence. The portion of a full double-stranded restriction enzyme recognition sequence may be of any restriction enzyme recognition sequence provided herein, including palindromic restriction enzyme recognition sequences. In some embodiments, the portion of a full double-stranded restriction enzyme recognition sequence is half of a palindromic double-stranded restriction enzyme recognition sequence. A "half" of a palindromic double-stranded restriction enzyme recognition sequence may include a half having a blunt-end or a half having a sticky end. As used herein, any configuration of an outermost portion of a stem may be described as a "half" of a full double-stranded restriction enzyme recognition sequence, if two of the halves combined together (e.g. by end-to-end ligation or annealing of two of the stems) form the corresponding full double-stranded restriction enzyme recognition sequence.

In some embodiments, inclusion of nucleotide sequences in an adaptor such that half of a full double-stranded restriction enzyme recognition sequence is formed at the outermost part of the stem of an adaptor may provide various different advantages. In some circumstances, use of an adaptor containing half of a full double-stranded restriction enzyme recognition sequence in the outermost part of the stem with a method provided herein may increase the efficiency of the amplification of the template or reduce background amplification. For example, a method provided herein may include a linear double-stranded nucleic acid template having at least one blunt end and an adaptor having a blunt-end half of double-stranded restriction enzyme recognition sequence at the outermost part of the stem of the adaptor (e.g. half of a StuI site). If two of the adaptors are ligated or otherwise joined end-to-end (i.e. outermost part to outermost part), a full double-stranded restriction enzyme recognition sequence is generated in the newly formed molecule (e.g. a full StuI site). If an enzyme which recognizes the full double-stranded restriction enzyme recognition sequence is present in the reaction with the newly formed molecule containing the two adaptor molecules joined end-to-end, it may recognize the full double-stranded restriction enzyme recognition sequence and cleave the newly formed molecule. This process may reduce or prevent the accumulation of undesirable adaptor self-ligation products. In contrast, if the adaptors is ligated to the end of the template, as long as the end of the template does not have a sequence which is half of the double-stranded restriction enzyme recognition sequence in the outermost part of the stem of the adaptor, the full double-stranded restriction enzyme recognition sequence will not be formed (e.g. a full StuI sequence will not be formed), and the adaptor-template ligation products will not be cleaved by the enzyme.

In some embodiments, in an adaptor containing a stem having an outermost part and an inner part, the inner part of the stem may contain a full double-stranded restriction enzyme recognition sequence. As used herein, these adaptors may be referred to as "recyclable adaptors". In certain embodiments, the full-double stranded restriction enzyme recognition sequence may begin a selected number of base pairs from the outermost base pair of the outermost part of the stem, such as 1, 2, 3, 4, 5, 6, 7, 8, 9, 10, 11, 12, 13, 14, 15 or more base pairs from the outermost base pair. In some embodiments, cleavage of the adaptor with a restriction enzyme which recognizes the full-double stranded restriction enzyme recognition sequence in the inner part of the stem results in the stem having a different outermost part than before the cleavage. For example, an adaptor may have a stem having an outermost part with sticky ends and an inner part containing the full double-stranded restriction enzyme sequence for the enzyme StuI. When cleaved by the StuI enzyme, a StuI sequence yields blunt ends. Accordingly, the adaptor may initially have a sticky end at the outermost part of the stem, but after cleavage of the adaptor with StuI (at the full StuI sequence in the inner part of the stem), the adaptor may have a blunt end at the new outermost part of the stem (i.e. the new outermost part of the stem may contain a portion of the StuI site which was cleaved). In another example, an adaptor may have a stem with an outermost part with sticky ends with a "TC" overhang on the 5' terminus, and the adaptor may also have the full double-stranded restriction enzyme sequence for the enzyme EcoRI in the inner part of the stem. When cleaved by the EcoRI enzyme, an EcoRI sequence yields an overhang "AATT" on the 5' strand. Accordingly, the adaptor may initially have a sticky end at the outermost part of the stem with a "TC" overhang on the 5' strand, but after cleavage of the adaptor with EcoRI, the adaptor may have a sticky end with an "AATT" overhang on the 5' strand at the new outermost part of the stem. A recyclable adaptor may further contain the single strand component of a restriction enzyme recognition sequence at any location in the adaptor. The single strand component of a restriction enzyme may correspond to the same or a different restriction enzyme than the full double-stranded restriction enzyme recognition sequence in the inner part of the stem of the adaptor.

In some embodiments, recyclable adaptors may be used with a method provided herein, where, after cleavage of the adaptor with the restriction enzyme which recognizes the full double-stranded restriction enzyme recognition sequence in the inner part of the stem, the new outermost part of the stem of the adaptor is complementary to or compatible with the ends of the linear double-stranded nucleic acid template. In some embodiments, the outermost part of a recyclable adaptor is not complementary to or compatible with the ends of a linear double-stranded nucleic acid template prior to cleavage of the adaptor with a restriction enzyme which recognizes the full double-stranded restriction enzyme recognition sequence in the inner part of the stem region of the adaptor. For example, if both ends of a linear double-stranded nucleic acid template have a blunt end, and the recyclable adaptor initially has a stem with an outermost part with sticky ends with a "TC" 5' overhang, the outermost part of the adaptor is not initially complementary to or compatible with the ends of the template (and therefore cannot bind to the template to form a circular strand). However, if the recyclable adaptor also contains a full double-stranded StuI site in the inner part of the stem, after cleavage of the adaptor with StuI, the new outermost part of the stem has a blunt end (i.e. half of the StuI site), which is compatible with the ends of the template.

In some embodiments, use of recyclable adaptors with methods provided herein may provide a number of advantages. In one example, use of recyclable adaptors may regulate the number of adaptors available to bind to each other and to the linear double-stranded nucleic acid template, thus helping to coordinate the number of available adaptor molecules with the number of available linear double-stranded nucleic acid template molecules. This may serve to reduce background non-specific amplification with methods provided herein. For example, in some circumstances, at the start of a method provided herein, there may be a greater number of adaptor molecules than linear double-stranded nucleic acid template molecules. If the adaptors can be joined end-to-end (e.g. by ligation), an undesirable amount of adaptor-adaptor ligation products might be formed in a method provided herein. However, if a recyclable adaptor having an outermost part having a sticky end with a "TC" 5' overhang and an inner part having a StuI site in the stem region is used in the method, initially, the adaptors having the outermost part having a sticky end with a 5' "TC" overhang will not be able to self-anneal or form adaptor-adaptor ligation products. Thus, the amount of non-specific background adaptor-adaptor ligation products generated will be minimized at the start of the reaction. If the recyclable adaptor is incubated with StuI, it will cleave some of the adaptors at the StuI site, yielding adaptors having a new outermost part having a blunt end. The blunt end is compatible with the ends of the linear double-stranded nucleic acid template, and therefore the cleaved recyclable adaptors will support generation of the circular strand in methods provided herein. The blunt ends of the outermost part of the stem of the cleaved recyclable adaptors will also support the formation of adaptor-adaptor ligation products. However, far fewer of these blunt-end adaptor-adaptor ligation products may be generated as compared to if all of the adaptors in the reaction already contained blunt ends at the outermost part of the stem at the start of the method. Also, in a circumstance where multiple cycles of a method provided herein are performed, since more double-stranded nucleic acids are being generated in each cycle of the method, as more recyclable adaptors having blunt ends become available (due to cleavage of the adaptor stems with StuI), more linear double-stranded nucleic acid templates are also available for the blunt end adaptors to bind. Accordingly, in some embodiments, the number of available template molecules may be at least generally coordinated with the number of adaptors available to bind to the template molecules (e.g. in methods provided herein using recyclable adaptors, as the number of linear double-stranded nucleic acid templates in the reaction increases, the number of adaptors which have been cleaved with the enzyme which recognizes the restriction enzyme sequence in the inner part of the stem also increases).

In some embodiments, an adaptor may be provided, wherein the adaptor is annealed to one or more additional nucleic acid strands. The additional nucleic acid annealed to the adaptor may serve any purpose. In some embodiments, the additional nucleic acid may aid in the detection of adaptor-dependent DNA replication. For example, the additional nucleic acid may contain a label that provides a different detectable signal depending on whether or not the additional nucleic acid is annealed to the adaptor. The additional nucleic acid may have any of the characteristics of a nucleic acid probe as described elsewhere herein (e.g. it may contain a fluorescent reporter and optionally, a quencher). In addition, the additional nucleic acid may be capable of being displaced by a polymerase having strand-displacement activity. Accordingly, if an adaptor is first connected to a linear double-stranded nucleic acid template during the generation of a circular strand, and a polymerase then synthesizes a first primer extension product along the length of the circular strand, once the polymerase encounters the additional nucleic acid annealed to the adaptor, it may displace the additional nucleic acid. This displacement may cause a change in a detectable signal from the label, which may be monitored. For example, the additional nucleic acid may contain a fluorophore at the 5' end and a quencher at the 3' end. These may be separated from each other when the additional nucleic acid is annealed to the adaptor (such that the fluorophore is not quenched) but positioned in close proximity to each other when the additional nucleic acid is not annealed to the adaptor (such that the fluorophore is quenched). Detection of a change in a detectable signal from the label may be correlated with polymerase activity along the adaptor nucleotides, and may be used to determine the rate or amount of nucleic acid amplification in a reaction described herein.

In some embodiments, a single type of adaptor may be used to amplify multiple different linear double-stranded nucleic acid templates. As described above and elsewhere herein, in some embodiments, during the formation of a circular strand, the adaptor does not anneal with any of the nucleotides of the linear double-stranded nucleic acid template (for example, if the template and the adaptors have blunt ends); instead, the adaptor only is ligated to the template. Accordingly, in some embodiments, a single type of adaptor provided herein may support the generation of a circular strand from an unlimited number of double-stranded templates. For example, an adaptor having a blunt end may support the amplification of any double-stranded template having blunt ends in a method provided herein, regardless of the sequence of the double-stranded template.

Adaptors may be prepared by a variety of methods. For example, adaptors may be prepared synthetically, using automated or conventional chemistry, such as by attaching a starting structure to beads and adding nucleotides thereto. Adaptors may also be prepared by synthesizing segments or fragments thereof and then joining the segments or fragments into larger adaptor structures containing appropriate nucleotide sequences for use as adaptors in compositions and methods provided herein. These segments or fragments may also be derived from microorganisms, such as from microorganisms which occur in nature or from microorganisms which contain cloned nucleotide sequences.

Primers

A "primer" as used herein may refer to a polynucleotide which is i) capable of hybridizing to a nucleic acid strand containing a nucleic acid template and ii) acting as a point of initiation for the synthesis of a new nucleic acid strand, wherein the new nucleic acid strand is an extension product of the primer and is complementary to a template strand. A primer may have a free —OH group at its 3' terminus, which may serve as the origin of synthesis for the extension product.

A primer may contain standard nucleotides [e.g. standard DNA deoxyribonucleotides (deoxyadenosine monophosphate, deoxyguanosine monophosphate, thymidine monophosphate, deoxycytidine monophosphate) or standard RNA ribonucleotides (adenosine monophosphate, guanosine monophosphate, uridine monophosphate, cytidine monophosphate)], alternative nucleotides (e.g. inosine), modified nucleotides, nucleotide analogs, or a combination thereof. For example, an oligonucleotide primer may include peptide nucleic acids, morpholinos (e.g. phosphorodiamidate morpholino oligos), locked nucleic acids [see, for example, Kaur, H, et. al, Biochemistry 45 (23), 7347-55 (2006)], glycol nucleic acids, or threose nucleic acids. A primer may have a backbone, including, for example, phosphodiester linkages, phosphorothioate linkages (a non-bridging O is replaced with sulfur), or peptide linkages (as part of a peptide nucleic acid). Alternative nucleotides, modified nucleotides, and nucleotide analogs may be referred to collectively herein as "non-standard nucleotides."

The presence of a non-standard nucleotide in a primer may affect various properties of the primer. In some embodiments, inclusion of a non-standard nucleotide in a primer may increase or decrease the thermodynamic stability of a primer to a complementary sequence thereof. For example, a primer having increased thermodynamic stability may contain a locked nucleic acid. A primer having decreased thermodynamic stability may contain, for example, inosine (described by Auer et al., Nucl. Acids Res. 24; 5021-5025 (1996)) or a negatively charged chemical group, such as a carboxylic acid.

A primer may be of any length and contain any nucleotide sequence which permits sufficiently stable and specific annealing of the primer to its complement at the temperature being used for a method involving the primer. The exact length desired of a primer may depend on a variety of factors, including the temperature of a reaction, the chemical composition of the primer, and the reaction involving the primer. In some examples, the primer may be at least 4, 5, 6, 7, 8, 9, 10, 12, 14, 16, 18, 20 or 25 nucleotides in length. In some examples, the primer may be no more than 4, 5, 6, 7, 8, 9, 10, 12, 14, 16, 18, 20, 25, 30, 35, 40, 45, or 50 nucleotides in length. Alternatively, the primer may be between 4 and 200, 5 and 200, 6 and 200, 7 and 200, 8 and 200, 9 and 200, 12 and 200, 14 and 200, 16 and 200, 18 and 200, 20 and 200, 25 and 200, 4 and 100, 5 and 100, 6 and 100, 7 and 100, 8 and 100, 9 and 100, 12 and 100, 14 and 100, 16 and 100, 18 and 100, 20 and 100, 25 and 100, 4 and 50, 5 and 50, 6 and 50, 7 and 50, 8 and 50, 9 and 50, 12 and 50, 14 and 50, 16 and 50, 18 and 50, 20 and 50, 25 and 50, 4 and 35, 5 and 35, 6 and 35, 7 and 35, 8 and 35, 9 and 35, 12 and 35, 14 and 35, 16 and 35, 18 and 35, 20 and 35, or 25 and 35 nucleotides in length. The inclusion of one or more non-standard nucleotides in the primer may change the desired length of the primer for use in a method provided herein, as compared to the length of a corresponding primer lacking a non-standard nucleotide. For example, if with a method provided herein it is desired to have a primer with a certain Tm, in some embodiments, a primer with the selected Tm may be of a shorter length if the primer contains at least some non-standard nucleotides, as compared to if the primer contains only standard nucleotides.

A primer provided herein may be prepared by any suitable method. For example, a primer may be chemically synthesized. In another example, a naturally occurring nucleic acid may be isolated, cleaved (e.g. with restriction enzymes), and/or modified to generate or to become part of a primer described herein.

In some embodiments, a label may be attached to a primer. Labels include, for example, binding ligands (e.g. digoxin or biotin), enzymes, fluorescent molecules/fluorphores, luminescent molecules, quencher molecules, or radioisotopes. In other embodiments, a base of an oligonucleotide may be replaced with a fluorescent analog, such as 2-aminopurine (see, for example, Proc. Acad. Sci. USA, 91, 6644-6648 (1994), which is herein incorporated by reference in its entirety).

Ligases

In some embodiments, a nucleic acid ligase is included with a method or composition provided herein. Ligases catalyze the formation of phosphodiester bonds between nucleotides, typically between the 5' phosphate of one nucleotide, and the 3' hydroxyl group of another nucleotide.

Nucleic acid ligases include *E. coli* DNA ligase, Taq DNA ligase, T3 DNA ligase, T4 DNA ligase, T7 DNA ligase, Ampligase™, T4 RNA ligase 1, and T4 RNA ligase 2.

In order to catalyze the ligation reaction, certain ligases require ATP (e.g. T4 DNA ligase) or NAD+ (*E. coli* DNA ligase). In some embodiments, a ligase may ligate nucleic acids having blunt ends. In some embodiments, a ligase may ligate nucleic acids having sticky ends. In some embodiments, a ligase may ligate nucleic acids having both blunt and sticky ends.

Modified versions ligases may also be used with the methods and compositions provided herein, provided that the modified ligase has the ability to catalyze the formation of phosphodiester bonds between nucleotides. A modified version of a ligase ("modified ligase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent, naturally occurring version of the ligase. In some embodiments, a modified ligase may contain no more than 1000, 700, 500, 400, 300, 200, 100, 50, 40, 30, 20, 10, or 5 greater or fewer amino acids than the parent ligase. In some embodiments, a modified ligase may comprise a fragment of a parent ligase. In some embodiments, a modified ligase may comprise a chimeric polypeptide with a portion derived from a ligase and a portion derived from a non-ligase protein. In some embodiments, a modified ligase may have, for example, increased catalytic activity, increased stability, or increased thermostability as compared to the parent ligase.

In some embodiments, a ligase provided herein is thermostable. A thermostable ligase may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified ligase may be thermostable.

In some embodiments, a ligase used with methods and compositions provided herein may be a modified ligase referred to herein as "p50-Tth", which has the amino acid sequence: mghhhhhhhhhhssghiegrasadgpylqileqpkqrg-frfryvcegpshgglpgasseknkksypqvkicnyvgpakvivqlvtng kni-hlhahslvgkhcedgictvtagpkdmvvgfanlgilhvtkkkvfetlearmtea-cirgynpgllvhpdlaylqaegggdrqlgdrek elirqaalqqtkemdlsvvrlmftaflpdstgsfirrlepvvsdalydskapnasn-lkivrmdrtagcvtggeelyllcdkvqkddiqirfte eeenggvwegfgdfspt-dvhrqfaivflapkykdinitkpasvfvqlrrksdletsepkpflyypeikd-keevqrkrqkgssgtsgggsgg gmtleearkrvnelrdliryhnyryvvladpeisdaeydrllrelkeleerfspelk-spdsptlqvgarpleatfrpvrhptrmysldnafnld elkafeerieralgrkgp-favtvehkvdglsvnlyveegvlvvgatrgdgevgeevtqnlltiptiprrlk-gvperlevrgevympieaflr lneeleergerifknprnaaagslrqkdpritakrglratfvalglgleevereg-vatqfallhwlkekgfpvehgvaravgaegveavyq dwlkkrralpfeadgv-vvkldelalwrelgytaraprfaiaykfpaeeketfildvvfqvgrtgrvtpvg-ilepvflegsevsrvtlhnesy ieeldirigdwvlvhkaggvipevlrylkerrtgeerpirw-petcpecghrllkegkvhrcpnplcpakrfeairhfasrkamdiqglge kli-erllekglvkdvadlyfirkedlvglermgeksaqnllrqieeskkrglerllyal-glpgvgevlarnlaarfgnmdrlleasleelleve evgeltarailetlkdpafrdlvrrlkeagvemeakekggealkgltfvitgelsr-preevkallrrlgakvtdsysrktsylvvgenpgskl ekaralgvptlteeelyrl-leartgkkaeelv (SEQ ID NO. 1). Ligase p50-Tth has thermostable blunt-end ligation activity at temperatures of at least 60 C. Ligase p50-Tth is a chimeric protein which comprises a His10-containing leader sequence ("His10" disclosed as SEQ ID NO:12), a p50 sequence from the human NF-kappa-B protein accession number NP_003989 amino acids 40-366 (indicated in italics), a flexible glycine rich sequence, and a Tth DNA ligase, from *Thermus Thermophilus* HB8, accession YP_144363 (indicated with under-lining). In some embodiments, a modified version of p50-Tth ligase may be used with methods and compositions provided herein (e.g. with 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acids from p50-Tth ligase).

Polymerases

In some embodiments, a nucleic acid polymerase is included with a method or composition provided herein. A polymerase may generate an extension product of a primer. The primer and extension product thereof may be complementary to a template nucleic acid strand. Generally, a polymerase will initiate synthesis of an extension product of a primer at the 3' end of the primer. In some embodiments, a DNA polymerase is included with a method or composition provided herein. As used herein, a "DNA polymerase" refers to a nucleic acid polymerase which has primary or exclusive polymerase activity on DNA templates. In some embodiments, a reverse transcriptase is included with a method or composition provided herein. As used herein, a "reverse transcriptase" refers to a nucleic acid polymerase which can synthesize a DNA strand from an RNA template.

In some embodiments, a polymerase provided herein may have strand displacement activity. Polymerases having strand displacement activity include, for example, exo-Bca DNA polymerase, phi29 DNA polymerase, Klenow Fragment of *E. coli* DNA Polymerase I, Vent$_R$ DNA polymerase, Deep VentR DNA polymerase, 9° N$_m$ DNA polymerase, and Large Fragment of Bst DNA Polymerase.

Modified versions of polymerases may also be used with the methods and compositions provided herein, provided that the modified polymerase has sequence-dependent nucleic acid synthesis activity. A modified version of a polymerase ("modified polymerase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent version of the polymerase. In some embodiments, a modified polymerase may contain no more than 1000, 700, 500, 400, 300, 200, 100, 50, 40, 30, 20, 10, or 5 greater or fewer amino acids than the parent polymerase. In some embodiments, a modified polymerase may comprise a fragment of a parent polymerase. In some embodiments, a modified polymerase may comprise a chimeric polypeptide with a portion derived from a polymerase and a portion derived from a non-polymerase protein. In some embodiments, a modified polymerase may have, for example, increased catalytic activity, increased stability, or increased thermostability as compared to the parent polymerase.

In some embodiments, a polymerase provided herein is thermostable. A thermostable polymerase may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified polymerase may be thermostable.

In some embodiments, a protein which binds to single-stranded nucleic acids (e.g. single-stranded binding protein (SSB), T4 Gene 34 protein) is provided in a method disclosed herein involving a polymerase having strand displacement activity. In some embodiments, generation of a new strand by a DNA polymerase having strand displacement activity may be increased by the addition of a single-stranded binding protein to the reaction.

Restriction Enzymes

In some embodiments, a restriction enzyme is included with a method or composition provided herein. Restriction enzymes generally cut double-stranded nucleic acids at or near a specific nucleotide sequence (a "restriction enzyme recognition sequence").

In some embodiments, a single type of restriction enzyme may be included with a method or composition provided herein. In other embodiments, two, three, four, five, or more types of restriction enzyme may be included with a method or composition provided herein. In some embodiments, in a method or composition provided herein involving an adaptor molecule containing restriction enzyme recognition sequences corresponding to 1, 2, 3, 4, 5, or more different restriction enzymes, the same number of types of restriction enzymes are provided as number of different types of restriction enzyme recognitions sequences in the adaptor molecule. For example, if an adaptor contains one single strand component of a restriction enzyme recognitions sequence corresponding to a first restriction enzyme and one full double-stranded restriction enzyme recognition sequence corresponding to a second restriction enzyme, two different restriction enzymes may be provided in compositions or methods involving the adaptor. In some embodiments, if two or more adaptors are provided in a method or composition provided herein, the same number of types of restriction enzymes are provided as number of different types of restriction enzyme recognitions sequences present in the two or more adaptors.

Restriction enzymes that may be used with methods or compositions provided herein include, for example, the enzymes AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FauI, Fnu4HI, FokI, FseI, FspEI, FspI, HaeII, HaeIII, HgaI, HhaI, HincII, HindIII, HinfI, HinPlI, HpaI, HpaII, HphI, Hpy166II, Hpy188I, Hpy188III, Hpy99I, HpyAV, HpyCH4III, HpyCH4IV, HpyCH4V, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, Taqα1, TfiI, TseI, Tsp45I, TspMI, TspRI, Tth111I, XbaI, XcmI, XhoI, XmaI, XmnI, or ZraI.

In some embodiments, one or more restriction enzymes which generate blunt ends from cleavage of a double-stranded nucleic acid may be used with a method or composition provided herein. Restriction enzymes which generate blunt ends include PvuII, SmaI, HaeIII, HgaI, AluI, EcoRV, ScaI, StuI, Acc113I, AccBSI, AcvI, AfaI, AfeI, AhaIII, AitI, Aor51HI, AosI, AspMI, AspNI, AssI, AviII, BalI, BanAI, BavI, BavAI, BavBI, BbrPI, BbvAI, BceBI, BcoAI, BecAII, BepI, Bim19II, Bme361I, BmgBI, BoxI, Bpu95I, BpuAmI, BsaAI, BsaBI, BscBI, Bse8I, BseQI, BshI, BsiBI, Bsp50I, Bsp68I, Bsp123I, BsrBI, BstUI, Cac8I, CcoI, CdiI, CeqI, CfuI, DmaI, DpnI, DraI, EcII, Eco32I, EgeI, FspI, HpaI, KspAI, MbiI, MlsI, MscI, MssI, NaeI, NmeRI, NruI, Pae17kI, PamI, Pde133I, PmaCI, PmeI, PmlI, PovII, PsiI, SarI, SauSI, SfaI, SmiI, SpoI, SruI, SspI, SuaI, SwaI, XcaI, XmnI, ZraI, and ZrmI.

Modified versions of any restriction enzyme provided herein may also be used with the methods and compositions provided herein, provided that the modified restriction enzyme has the ability to recognize and cleave a specific double-stranded nucleic acid sequences. A modified version of a restriction enzyme ("modified restriction enzyme") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent version of the restriction enzyme. In some embodiments, a modified restriction enzyme may contain no more than 1000, 700, 500, 400, 300, 200, 100, 50, 40, 30, 20, 10, or 5 greater or fewer amino acids than the parent restriction enzyme. In some embodiments, a modified restriction enzyme may comprise a fragment of a parent restriction enzyme. In some embodiments, a modified restriction enzyme may comprise a chimeric restriction enzyme with a portion derived from a restriction enzyme and a portion derived from a non-restriction enzyme protein. In some embodiments, a modified restriction enzyme may have, for example, increased catalytic activity, increased stability, or increased thermostability as compared to the parent restriction enzyme.

In some embodiments, a restriction enzyme provided herein is thermostable. A thermostable restriction enzyme may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified restriction enzyme may be thermostable.

Vessels

In some embodiments, provided herein is a vessel containing one or more enzymes, primers, adaptors, or other reagents provided herein. Vessels may include any structure capable of supporting or containing a liquid or solid material and may include, tubes, containers, tips, etc. In some embodiments, a wall of a vessel may permit the transmission of light through the wall. A vessel may be optically clear. A vessel may contain, for example, any one or more of an isolated nucleic acid ligase, an isolated nucleic acid polymerase, an isolated DNA polymerase, an isolated reverse transcriptase, an isolated restriction enzyme, an adaptor, a first primer complementary to a complementary strand of a double stranded nucleic acid template of interest, or a second primer complementary to a complementary strand of a double stranded nucleic acid template of interest, a nucleic acid dye, or a nucleic acid probe, as described elsewhere herein. The contents of a vessel may be in fluid communication. In some embodiments, a vessel may further contain a linear double-stranded nucleic acid template. In some embodiments, a vessel may further contain nucleotides, buffers, salts, water, or other reagents provided herein for the amplification of nucleic acids. In some embodiments, a vessel may contain two or more sets of primers, wherein each primer set comprises a first and second primer, and the different primer sets are complementary to different target nucleic acids.

Kits

Two or more reagents useful for a method provided herein may be packaged and provided as a kit. For example, a kit may include any two or more of: a linear double stranded nucleic acid template, an adaptor, a first primer complementary to a complementary strand of a double stranded nucleic acid template of interest, a second primer complementary to a complementary strand of a double stranded nucleic acid template of interest, a ligase, a DNA polymerase, a restriction enzyme, buffers, a nucleic acid dye, a nucleic acid probe, a reverse transcriptase, or dNTPs, as described elsewhere herein. Within the kit, the two or more reagents may be packaged in separate vessels or the same vessel. In some embodiments, a kit may further contain nucleotides, buffers, salts, water, or other reagents provided herein for the amplification of nucleic acids.

Applications

The various methods and compositions provided herein for amplification of a target nucleic acid sequence can fulfill many of the functions that have previously been carried out by other methods and compositions for isothermal and thermocycler-dependent nucleic acid amplification. Amplification methods and compositions provided herein may be used, for example, for isolation and cloning of nucleic acids of interest, gene expression analysis, diagnostic identification of nucleic acids, synthesis of novel nucleic acids, nucleic acid probe synthesis and labeling, forensic identification of a subject, allele identification from a subject, genetic screening, nucleic acid sequencing, and related applications. A target nucleic acid molecule may be of any type, including single-stranded or double stranded and DNA or RNA (e.g. mRNA).). A target nucleic acid may be of any type or function (e.g. a protein-coding sequence, a regulatory sequence, an intron, etc.). A target nucleic acid may be the entirety of a gene, or a portion thereof. Methods provided herein may include conversion of a single strand nucleic acid target molecule to a linear double-stranded nucleic acid template by methods disclosed herein or otherwise known in the art.

In some embodiments, a method or composition provided herein may be used to detect the amount of a target nucleic acid in a sample (including the presence or absence of the target), to measure the amount of an amplification product of a target formed from a sample in a selected period of time, or to determine the amount of time necessary to generate a certain number of copies of a template from a sample. Samples which may be used with methods and compositions provided herein are described elsewhere herein, and may include, for example, a bodily fluid, a secretion, or a tissue of a subject.

In some embodiments, a method provided herein may be performed to simultaneously assay for at least 2, 3, 4, 5, 6, 7, 8, 9, 10, 12, 15, 20, 25, 30, 35, 40, 45, 50, 75, 100, or more different target nucleic acids in the same reaction vessel. Typically, for each target nucleic acid of interest, a first primer and a second primer are provided, each being complementary to a strand of the nucleic acid target, or a complement thereof. The amplification of the different target nucleic acids in the same vessel may be monitored, for example, by the use of nucleic acid probes having sequence specificity for detection sequences in the different target nucleic acids, and different fluorophores.

In some embodiments, a method or composition provided herein may be used to detect the presence or absence of a particular nucleotide of interest in a target nucleic acid (e.g. in the case of a mutation or SNP). For example, a first or second primer may be selected which selectively binds to a region in a target nucleic acid which includes or is adjacent to the nucleotide of interest. The primer may be designed such that it selectively either: i) binds to the region when the region contains the nucleotide of interest, or ii) does not bind to the region when the region contains the nucleotide of interest. A method as described herein may be performed with the selected primer, and the outcome of the amplification reaction may provide information regarding the presence or absence of the nucleotide of interest in the target nucleic acid. For example, if a first primer is designed to have a nucleotide sequence which is complementary to a sequence in the target nucleic acid which includes a particular nucleotide of interest (e.g. a mutation), successful amplification of the target nucleic acid with the selected primer from a sample may indicate that the sample contains a target nucleic acid having the particular nucleotide of interest. In some embodiments, a primer used for analysis of a nucleotide of interest in a target nucleic acid may contain a critical nucleotide at the 3' terminus of the primer. In such a case, the annealing of the final 3' nucleotide of the primer may be dependent on the presence of the nucleotide of interest in the target nucleic acid. If the final 3' nucleotide of the primer does not anneal with a nucleotide in the target nucleic acid (e.g. due to a mismatch between the nucleotides), the mismatch may significantly impair a nucleic acid polymerase from synthesizing an extension product from the primer. Accordingly, in some embodiments, a primer having a 3' terminal nucleotide which corresponds to a nucleotide of interest may be useful for determining the presence or absence of a particular nucleotide in a target nucleic acid.

Methods and compositions provided herein may be used to amplify a nucleic acid from any sample which may contain nucleic acids. Examples of samples may include various fluid samples. In some instances, the sample may be a bodily fluid sample from a subject. The sample may include one or more fluid component. In some instances, solid or semi-solid samples may be provided. The sample may include tissue collected from the subject. The sample may include a bodily fluid, secretion, or tissue of a subject. The sample may be a biological sample. The biological sample may be a bodily fluid, a secretion, or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. The sample may be provided from a human or animal. Samples may be from a plant, microorganism (e.g. virus, bacteria), or other biological material.

In some embodiments, methods and compositions provided herein may be performed at or used at point of service locations (e.g. a subject's home or work, grocery stores, drug stores, clinics, schools, etc.). Methods and compositions provided herein may permit the rapid amplification of nucleic acids in a sample from a subject, in order to aid in the diagnosis or treatment of a subject.

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or perform a method with one or more reagents, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. A cartridge may contain reagents disclosed herein for the performing a method disclosed herein. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in nonliquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assays on a sample, and to obtain data from the sample. A sample processing device may perform methods provided herein, as well as additional assays. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In some embodiments, a sample processing device may be configured to perform a method provided herein and one, two, or more additional assays. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte (e.g. a target nucleic acid) or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay (e.g. methods provided herein), receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Description and disclosure of examples of reagents, assays, methods, kits, devices, and systems which may use, or be used with, methods, compositions, or other reagents disclosed herein may be found, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

EXAMPLES

The following examples are offered for illustrative purposes only, and are not intended to limit the present disclosure in any way.

Example 1

Amplification of a Linear Double-Stranded Nucleic Acid Generated from a Target Single Strand RNA Molecule A target single strand RNA molecule was converted to a linear double-stranded nucleic template and amplified according to a method provided herein. 25 microliter reaction mixtures were prepared, each containing: 50 mM potassium acetate, 20 mM Tris-acetate, pH 7.9, 10 mM magnesium acetate, 1 mM DTT, 5 µg bovine serum albumin (BSA), 0.1 µM adaptor molecule "EE0162" [nucleotide sequence (including a 5' phosphate): 5' GGGATCATCATCCAAGTACTTGGATGATGATCCC 3' (SEQ ID NO:2)], 1.4 mM each of dATP, dTTP, dGTP, and dCTP, 0.5% volume/volume polyethylene glycol (PEG)–6000, 2 mM SYTO® 59 (Life Technologies), 200 units T4 DNA ligase (New England Biolabs), 25 units restriction enzyme ScaI (New England Biolabs), 25 units phi29 DNA polymerase (New England Biolabs), 25 units murine RNase inhibitor (New England Biolabs), 0.1 unit AMV reverse trancriptase enzyme (New England Biolabs), 0.8 µM primer "RLX82" [nucleotide sequence: 5' AATTCTCTTTAAATAAACCCA 3' (SEQ ID NO:3), where the underlined nucleotides are locked nucleic acid nucleotides (Exiqon)], 0.8 µM primer "RLX30" (nucleotide sequence: 5' GACACAATCTGCATGAAATC 3' (SEQ ID NO:4), where the underlined nucleotides are locked nucleic acid nucleotides), 1 mM rATP ribonucleotide triphosphate, and 0, 2,500, 25,000, or 250,000 copies target RNA molecule per microliter. The target RNA is an RNA copy of a strand of a Major Outer Membrane Protein (MOMP) gene, TOR1, from Chlamydia pneumonia. The RNA was prepared from the TOR1 DNA sequence below (i.e. the RNA was complementary to the following sequence): 5' AATTCTCTTTAAATAAACCCAAGGGCTATAAGGCGTTGCTTTCCCTTTGCCAACAG ATGCTGGCGTAGTAACAGCTGCTGAACAAAGTCTGCGACCATCAATTATCATGAATGGCAGGTAGGAGCCTCTCTATCTTATAGACTCAACTCTTTAGTGCCATACATTGGAG TCCAATGGTCTCGAGCAACTTTTGATGCTGATAACATCCGCATGCTCAGCCAAAGCTACCTACAGCTATTTTAAACTTAACTGCATGGAAC CCTTCTTTACTAGGGAGTGCCA CAGCTGTTTCTTCATCTGATCAATTCTCAGATTTCATGCAGATTGTGTC 3' (SEQ ID NO:5). The adaptor molecule EE0162 has a nucleotide sequence capable for forming a stem-loop structure, where the stem contains 15 nucleotide pairs (Tm 35 C) and the loop contains 4 nucleotides. EE0162 contains the single-strand component of a restriction enzyme sequence for the restriction enzyme ScaI (5'AGTACT 3'); the middle 4 nucleotides of this sequence (GTAC) are located in the loop region of the adaptor, and the outer A and T of the sequence are in the stem region (where they may pair to each other). The reaction mixtures were prepared in triplicate for each different amount of RNA template. For each reaction, the rATP and chlamydia RNA template were added to the mixture last, which served as the initiation point of the reaction. In the reaction mixture, the RNA was converted to a linear double-stranded DNA template, which was amplified according to a method provided herein. Upon initiation of the reactions, the reactions (assays) were continuously monitored for 120 minutes for fluorescence at excitation/emission wavelengths of 620/650 nm in a CFX 96 Touch instrument (Bio-Rad). The reactions were performed at 38.5 C. FIG. 2 shows results from the reactions. The X-axis shows time (minutes) and the Y-axis shows Reference Fluorescence Units (RFU; 10^3)). Reactions containing different amounts of target RNA nucleotides are marked with different letters: "A"=250,000 copies, "B"=25,000 copies, "C"=2,500 copies, D=0 copies of the target molecule. As shown in FIG. 2, the 250,000 target copy reactions had a signal above background (6 RFU) by about 35 minutes, the 25,000 target copy reactions had a signal above background by about 40 minutes, and the 2,500 target copy reactions had a signal above background by about 60 minutes. The 0 target molecule control did not generate a signal significantly above background after 120 minutes.

Example 2

Figure 3:
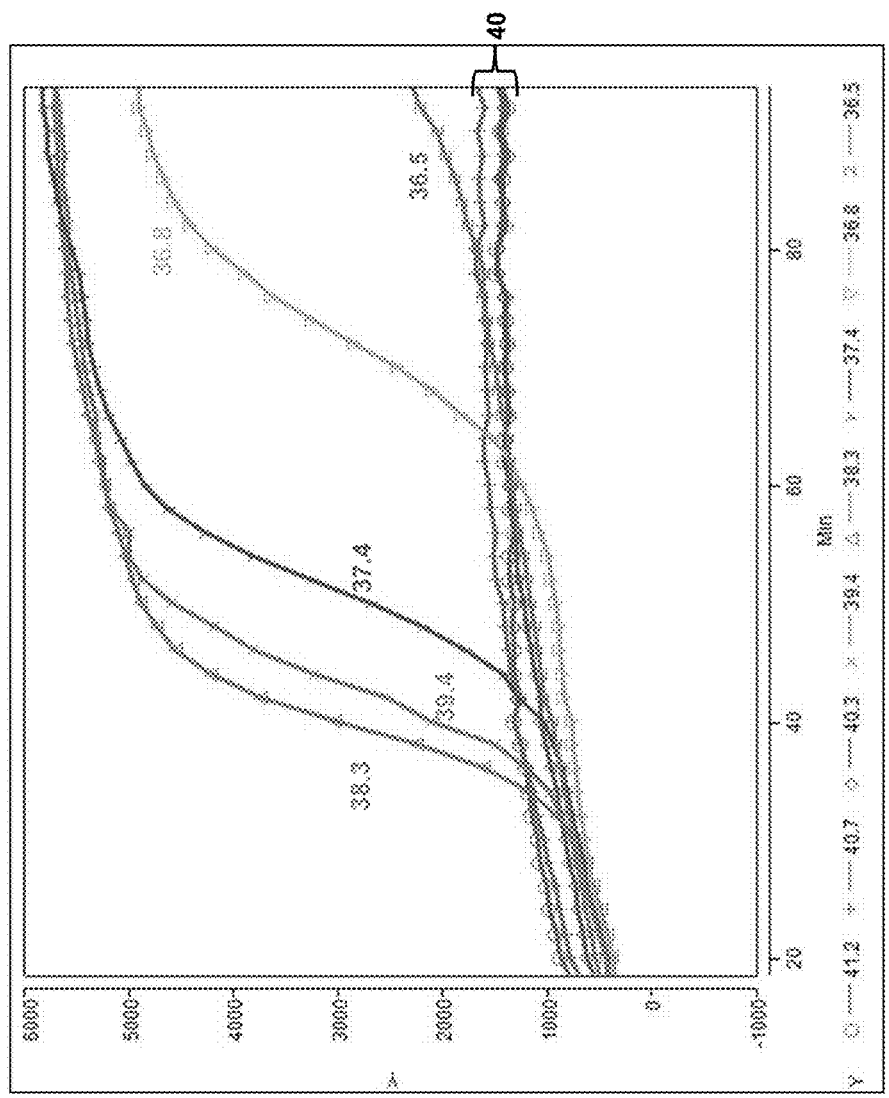
FIG. 3 is a graph depicting results from reactions performed according to a method provided herein.
Figure 4:
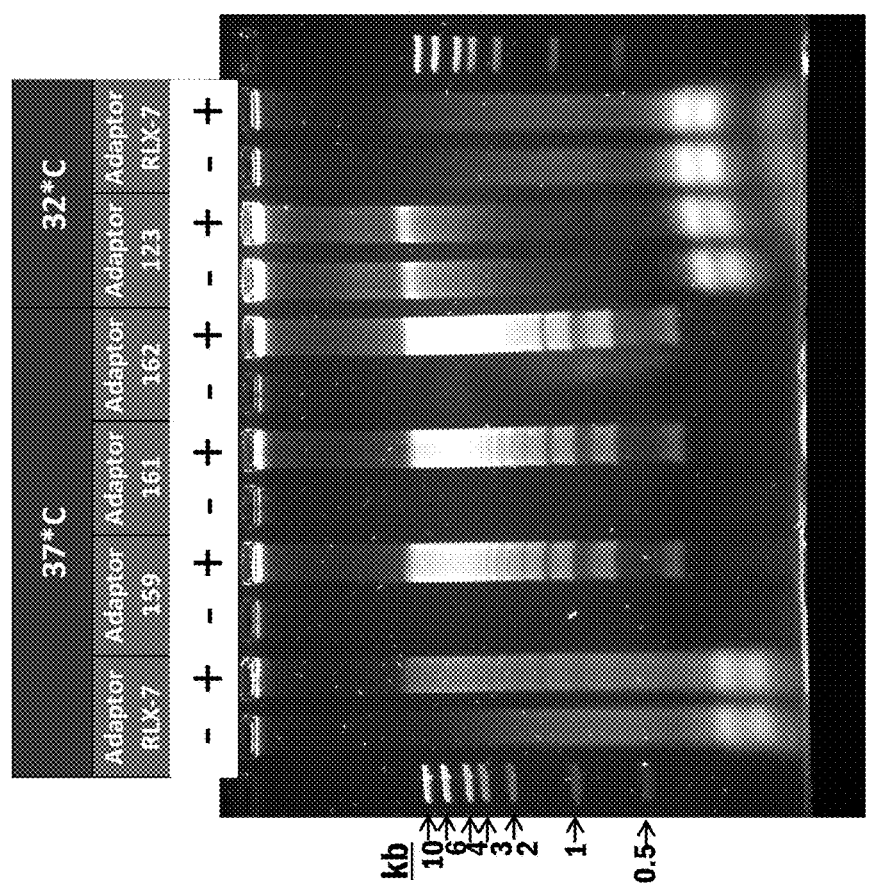
FIG. 4 is an image of an agarose gel containing samples of reactions performed according to a method provided herein.

Amplification of a Target Linear Double Stranded DNA Molecule: Different Temperatures A target linear double stranded DNA was amplified according to a method provided herein. 25 microliter reaction mixtures were prepared, each containing: 50 mM potassium acetate, 20 mM Tris-acetate, pH 7.9, 10 mM magnesium acetate, 1 mM DTT, 5 µg bovine serum albumin (BSA), 0.05 µM adaptor molecule "EE0162" [nucleotide sequence (including a 5' phosphate): 5' GGGATCATCATCCAAGTACTTGGATGATGATCCC 3' (SEQ ID NO:2)], 1.4 mM each of dATP, dTTP, dGTP, and dCTP, 0.4×SYBR® Green (Life Technologies), 200 units T4 DNA ligase (New England Biolabs), 18 units restriction enzyme ScaI (New England Biolabs), 25 units phi29 DNA polymerase (New England Biolabs), 1 µM primer "RLX82" [nucleotide sequence: 5' AATTCTCTTTAAATAAACCCA 3' (SEQ ID NO:3), where the underlined nucleotides are locked nucleic acid nucleotides (Exiqon)], 1 µM primer "RLX142" (nucleotide sequence: 5' GACACAATCTGCATGAAATC 3' (SEQ ID NO:6), where the underlined nucleotides are locked nucleic acid nucleotides), 1 mM rATP ribonucleotide triphosphate, and 1,000,000 copies per microliter target Chlamydia pneumonia TOR1 linear double-stranded DNA molecule (a strand having the sequence provided above in Example 1). 16 reaction mixtures having the composition listed above were prepared, and 2 of these mixtures were incubated at each of: 36.5, 36.8, 37.4, 38.3, 39.4, 40.3, 40.7, and 41.2 C. Upon the initiation of the reactions, the assays were continuously monitored for 100 minutes for fluorescence at excitation/emission wavelengths of 494/521 nm in a CFX Touch instrument (Bio-Rad). FIG. 3 shows results from the reactions, where the plot for each different reaction temperature is the average of the two reactions performed at each temperature. The X-axis shows time (minutes) and the Y-axis shows Reference Fluorescence Units. As shown in FIG. 3, the optimal temperature for the reaction with these reagents was between 37.4 and 39.4 C., with peak activity at 38.3 C.

Example 3

Amplification of Target Linear Double Stranded DNA Molecule: Different Quantity Template A target linear double stranded DNA was amplified according to a method provided herein. 25 microliter reaction mixtures were prepared, each containing: 50 mM potassium acetate, 20 mM Tris-acetate, pH 7.9, 10 mM magnesium acetate, 1 mM DTT, 5 µg bovine serum albumin (BSA), 0.08 µM adaptor molecule "EE0162" [nucleotide sequence (including a 5' phosphate): 5' GGGATCATCATCCAAGTACTTGGATGATGATCCC 3' (SEQ ID NO:2)], 1.4 mM each of dATP, dTTP, dGTP, and dCTP, 0.4×SYBR® Green (Life Technologies), 200 units T4 DNA ligase (New England Biolabs), 18 units restriction enzyme ScaI (New England Biolabs), 25 units phi29 DNA polymerase (New England Biolabs), 1 µM primer "RLX82" [nucleotide sequence: 5' AATTCTCTTTAAATAAACCCA 3' (SEQ ID NO:3), where the underlined nucleotides are locked nucleic acid nucleotides (Exiqon)], 1 µM primer "RLX30" (nucleotide sequence: 5' GACACAATCTGCATGAAATC 3' (SEQ ID NO:4), where the underlined nucleotides are locked nucleic acid nucleotides, 1 mM rATP ribonucleotide triphosphate, 0.5% volume/volume polyethylene glycol (PEG)–6000, and 0, 1, 10, 100, 1,000 or 10,000 copies per microliter target Chlamydia pneumonia TOR1 linear double-stranded DNA molecule (a strand having the sequence provided above in Example 1). 16 reaction mixtures having the composition listed above were prepared for each of the different amounts of target chlamydia linear double-stranded DNA template. Upon the initiation of the reactions, the assays were continuously monitored for 120 minutes for fluorescence at excitation/emission wavelengths of 494/521 nm in a CFX Touch instrument (Bio-Rad). The reactions were incubated at 38.5 C. Table 1 shows the results from the assays, listing the average time for inflection ("Ave Tinf") (i.e. positive signal) of the assays with the different quantities of target nucleic acid. The inflection point of the assays was determined based on analysis of the reactions with CFX Manager software (Bio-Rad). Reactions with 10 copies or less of the target nucleic acid molecule did not generate a positive inflection point, and are not listed in the Table. Table 1 also lists the Standard Deviation of inflection time for the assays with the different quantities of target nucleic acid. As shown in Table 1, methods provided herein can efficiently amplify a target nucleic acid from a reaction containing 100 copies of target nucleic acid molecule per microliter or lower.

TABLE 1

| Copy # | Avg Tinf (min) | St Dev |
|---|---|---|
| 10,000 | 39.16 | 2.47 |
| 1,000 | 51.02 | 4.92 |
| 100 | 77.16 | 17.15 |

Example 4

Amplification of Target Linear Double Stranded DNA Molecule: Different Adaptors

A target linear double stranded DNA was amplified according to a method provided herein. 20 microliter reaction mixtures were prepared, each containing: 50 mM potassium acetate, 20 mM Tris-acetate, pH 7.9, 10 mM magnesium acetate, 1 mM DTT, 4 µg bovine serum albumin (BSA), 1.4 mM each of dATP, dTTP, dGTP, and dCTP, 400 units T4 DNA ligase (New England Biolabs), 20 units restriction enzyme ScaI (New England Biolabs), 28 units phi29 DNA polymerase (New England Biolabs), 0.8 µM primer "EE0146" [nucleotide sequence: 5' AATTCTCTTTAAATAAACCCA (SEQ ID NO:3), where the underlined nucleotides are locked nucleic acid nucleotides (Exiqon)] 0.8 µM primer "EE0147" [nucleotide sequence: 5' GACACAATCTGCATGAAATC (SEQ ID NO:7), where the underlined nucleotides are locked nucleic acid nucleotides (Exiqon)], 1 mM rATP ribonucleotide triphosphate, 0.5 µM adaptor molecule selected from: "RLX0007" "RLX-7" (nucleotide sequence: 5' GGGATCATCAGCCTAGAAAAAAAAAAAAAAAAAAAAAGTACTTAAAAAAAAATAGGCT GATGATCCC 3') (SEQ ID NO:8), "EE0159"/"159" (nucleotide sequence: 5' GGGATCATCATCACATAGTACTATGTGATGATGATCCC 3') (SEQ ID NO;9), "EE0161"/"161" (nucleotide sequence: GGGATCATCATCCATCAGTACTGATGGATGATGATCCC 3') (SEQ ID NO:10), "EE0162"/"162" (nucleotide sequence: 5' GGGATCATCATCCAAGTACTTGGATGATGATCCC 3') (SEQ ID NO:2), and "EE0123"/"123" (nucleotide sequence: 5' GGGATCATCAGCCTAGTCAGTCAGTCATTCATTCAGTACTTCAGTCAGTTAGGCTGA TGATCCC 3') (SEQ ID NO:11), and optionally, 1,000,000 copies per microliter target Chlamydia pneumonia TOR1 linear double-stranded DNA molecule (a strand having the sequence provided above in Example 1). The adaptor molecule RLX-7 has a nucleotide sequence capable of forming a stem-loop structure, where the stem contains 15 nucleotide pairs and the loop contains 34 nucleotides. The adaptor molecule 159 has a nucleotide sequence capable for forming a stem-loop structure, where the stem contains 17 nucleotide pairs (Tm 37 C) and the loop contains 4 nucleotides. The adaptor molecule 161 has a nucleotide sequence capable for forming a stem-loop structure, where the stem contains 17 nucleotide pairs (Tm 42 C) and the loop contains 4 nucleotides. The adaptor molecule 162 has a nucleotide sequence capable for forming a stem-loop structure, where the stem contains 15 nucleotide pairs (Tm 35 C) and the loop contains 4 nucleotides. The adaptor molecule 123 has a nucleotide sequence capable for forming a stem-loop structure, where the stem contains 15 nucleotide pairs and the loop contains 35 nucleotides. A reaction with and without template molecules was prepared for each of the different adaptors; two reactions with and without template molecules were prepared for the adaptor RLX-7. The reactions were incubated at either 37 C or 32 C for 45 minutes (37 C: reactions with adaptors RLX-7, 159, 161, and 162; 32 C: reactions with adaptors RLX-7 and 123), and then heat inactivated at 80 C for twenty minutes. Then, each reaction mixture was loaded on an agarose gel, separated on the gel, and stained with SYBR® gold (Life Technologies). As indicated on the gel, the reactions with the 159, 161, and 162 adaptors effectively amplified the linear double stranded nucleic acid template. Marker standards are shown on the left and right sides of the gel. The various bands in the reactions with the 159, 161 and 162 adaptors show reaction products containing 1, 2, 3, or more copies of the TOR1 template.

While preferred embodiments of the present invention have been shown and described herein, it will be obvious to those skilled in the art that such embodiments are provided by way of example only. The foregoing description is not intended to be exhaustive or to limit the invention to the precise embodiments disclosed, and other modifications and variations may be possible in light of the above teachings without departing from the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013 Theranos, Inc.

I claim:

1. A method for amplifying a linear double-stranded nucleic acid template comprising two separate complementary strands, comprising:
   (A) ligating an adaptor comprising a single nucleic acid strand to each end of a linear double-stranded nucleic acid template, to yield a circular strand containing the general formula in the 5' to 3' direction: -A1-S1-A2-S2-, wherein
      each adaptor contains at least four nucleotide bases and a single strand component of a restriction enzyme recognition sequence,
      A1 and A2 denote separate adaptors,
      S1 denotes a first complementary strand of the linear double-stranded nucleic acid template,
      S2 denotes a second complementary strand of the linear double-stranded nucleic acid template,
      the 3' terminus of A1 is linked to the 5' terminus of S1,
      the 3' terminus of S1 is linked to the 5' terminus of A2,
      the 3' terminus of A2 is linked to the 5' terminus of S2, and
      the 3' terminus of S2 is linked to the 5' terminus of A1;
   (B) annealing a first oligonucleotide primer to the circular strand;
   (C) extending the first oligonucleotide primer along the circular strand by using a polymerase, to form an extension product of the first primer;
   (D) annealing a second oligonucleotide primer to the extension product of the first primer;
   (E) extending the second oligonucleotide primer along at least a portion of the extension product of the first primer by using a polymerase, to produce a new double-stranded nucleic acid comprising at least a portion of the extension product of the first primer and at least a portion of the extension product of the second primer;
   (F) cleaving the new double-stranded nucleic acid of step with a restriction enzyme that recognizes a full double-stranded restriction enzyme recognition sequence corresponding to the single strand component of a restriction enzyme sequence of at least one of the adaptors, to form two or more shorter double-stranded nucleic acids, at least two of which comprise at least a portion of a copy of the linear double-stranded nucleic acid template of step (A), thereby amplifying the linear double-stranded nucleic acid template; and
   (G) repeating steps (A)-(F) for one or more additional cycles, using the double stranded nucleic acid of step (F) of a first cycle as the linear double-stranded nucleic acid template of step (A) of a second cycle.

2. The method of claim 1, wherein at least two of the shorter double-stranded nucleic acids contain a complete copy of the linear double-stranded nucleic acid template of step (A).

3. The method of claim 1, further comprising wherein steps (B) and (C) of the second cycle comprises treating at least two different circular strands with the first oligonucleotide primer and polymerase, wherein the at least two different circular strands comprise: i) a circular strand formed in the first cycle and ii) a circular strand formed in the second cycle.

4. The method of claim 1, wherein the first oligonucleotide primer is complementary to a complementary strand of the linear double-stranded nucleic acid template.

5. The method of claim 1, wherein the second oligonucleotide primer is complementary to a complementary strand of the linear double-stranded nucleic acid template.

6. The method of claim 1, wherein both the first oligonucleotide primer and the second oligonucleotide primer are complementary to a complementary strand of the linear double-stranded nucleic acid template, and wherein the first oligonucleotide primer and the second oligonucleotide primer are complementary to different strands of the linear double-stranded nucleic acid template.

7. The method of claim 1, wherein at least one of the first oligonucleotide primer or the second oligonucleotide primer is complementary to at least one of the adaptors.

8. The method of claim 1, wherein the adaptors contain single strand components of a restriction enzyme recognition sequence corresponding to the same restriction enzyme.

9. The method of claim 1, wherein the adaptors contain single strand components of a restriction enzyme recognition sequence corresponding to different restriction enzymes.

10. The method of claim 1, wherein at least one of the adaptors contains a nucleotide sequence comprising a 5' region, a middle region, and a 3' region, wherein the 5' region and 3' region of the sequence are complementary to each other such that under certain conditions they anneal to each other and form the stem of a stem-loop structure, and wherein the stem contains a blunt end.

11. The method of claim 1, wherein at least one of the adaptors contains a nucleotide sequence comprising a 5' region, a middle region, and a 3' region, wherein the 5' region and 3' region of the sequence are complementary to each other and capable of annealing to each other and form the stem of a stem-loop structure, and wherein the outermost part of the stem contains a sticky end.

12. The method of claim 1, wherein at least one of the adaptors contains a nucleotide sequence comprising a 5' region, a middle region, and a 3' region, wherein the 5' region and 3' region of the sequence are complementary to each other and capable of annealing to each other and form the stem of a stem-loop structure, and wherein the outermost part of the stem contains half of a full double-stranded restriction enzyme recognition sequence.

13. The method of claim 1, wherein the polymerase which generates the extension product of the first primer has strand displacement activity.

14. The method of claim 1, wherein the polymerase which generates the extension product of the second primer has strand displacement activity.

15. The method of claim 1, wherein all steps of the method are performed at a temperature of no greater than 70-° C.

16. The method of claim 1, wherein all steps of the method are performed at a temperature of no greater than 60-° C.

17. The method of claim 1, wherein all steps of the method are performed at a temperature of no greater than 50-° C.

18. The method of claim 1, wherein all steps of the method are performed at a temperature of no greater than 40-° C.

19. The method of any of claim 1, wherein the linear double-stranded nucleic acid template is amplified at least 10-fold within 60 minutes of initiation of the method.

* * * * *

SEQUENCE LISTING

```
<160> NUMBER OF SEQ ID NOS: 12

<210> SEQ ID NO 1
<211> LENGTH: 1038
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly His His His His His His His His Ser Ser Gly His
1               5                   10                  15

Ile Glu Gly Arg Ala Ser Ala Asp Gly Pro Tyr Leu Gln Ile Leu Glu
            20                  25                  30

Gln Pro Lys Gln Arg Gly Phe Arg Phe Arg Tyr Val Cys Glu Gly Pro
        35                  40                  45

Ser His Gly Gly Leu Pro Gly Ala Ser Ser Glu Lys Asn Lys Lys Ser
    50                  55                  60

Tyr Pro Gln Val Lys Ile Cys Asn Tyr Val Gly Pro Ala Lys Val Ile
65                  70                  75                  80

Val Gln Leu Val Thr Asn Gly Lys Asn Ile His Leu His Ala His Ser
                85                  90                  95

Leu Val Gly Lys His Cys Glu Asp Gly Ile Cys Thr Val Thr Ala Gly
                100                 105                 110

Pro Lys Asp Met Val Val Gly Phe Ala Asn Leu Gly Ile Leu His Val
            115                 120                 125

Thr Lys Lys Lys Val Phe Glu Thr Leu Glu Ala Arg Met Thr Glu Ala
        130                 135                 140

Cys Ile Arg Gly Tyr Asn Pro Gly Leu Leu Val His Pro Asp Leu Ala
145                 150                 155                 160

Tyr Leu Gln Ala Glu Gly Gly Gly Asp Arg Gln Leu Gly Asp Arg Glu
                165                 170                 175

Lys Glu Leu Ile Arg Gln Ala Ala Leu Gln Gln Thr Lys Glu Met Asp
```

```
                180                 185                 190
Leu Ser Val Val Arg Leu Met Phe Thr Ala Phe Leu Pro Asp Ser Thr
            195                 200                 205
Gly Ser Phe Thr Arg Arg Leu Glu Pro Val Val Ser Asp Ala Ile Tyr
            210                 215                 220
Asp Ser Lys Ala Pro Asn Ala Ser Asn Leu Lys Ile Val Arg Met Asp
225                 230                 235                 240
Arg Thr Ala Gly Cys Val Thr Gly Gly Glu Glu Ile Tyr Leu Leu Cys
                245                 250                 255
Asp Lys Val Gln Lys Asp Asp Ile Gln Ile Arg Phe Tyr Glu Glu Glu
                260                 265                 270
Glu Asn Gly Gly Val Trp Glu Gly Phe Gly Asp Phe Ser Pro Thr Asp
                275                 280                 285
Val His Arg Gln Phe Ala Ile Val Phe Lys Thr Pro Lys Tyr Lys Asp
                290                 295                 300
Ile Asn Ile Thr Lys Pro Ala Ser Val Phe Val Gln Leu Arg Arg Lys
305                 310                 315                 320
Ser Asp Leu Glu Thr Ser Glu Pro Lys Pro Phe Leu Tyr Tyr Pro Glu
                325                 330                 335
Ile Lys Asp Lys Glu Glu Val Gln Arg Lys Arg Gln Lys Gly Ser Ser
                340                 345                 350
Gly Thr Ser Gly Gly Gly Ser Gly Gly Met Thr Leu Glu Glu Ala
                355                 360                 365
Arg Lys Arg Val Asn Glu Leu Arg Asp Leu Ile Arg Tyr His Asn Tyr
            370                 375                 380
Arg Tyr Tyr Val Leu Ala Asp Pro Glu Ile Ser Asp Ala Glu Tyr Asp
385                 390                 395                 400
Arg Leu Leu Arg Glu Leu Lys Glu Leu Glu Arg Phe Pro Glu Leu
                405                 410                 415
Lys Ser Pro Asp Ser Pro Thr Leu Gln Val Gly Ala Arg Pro Leu Glu
                420                 425                 430
Ala Thr Phe Arg Pro Val Arg His Pro Thr Arg Met Tyr Ser Leu Asp
            435                 440                 445
Asn Ala Phe Asn Leu Asp Glu Leu Lys Ala Phe Glu Glu Arg Ile Glu
            450                 455                 460
Arg Ala Leu Gly Arg Lys Gly Pro Phe Ala Tyr Thr Val Glu His Lys
465                 470                 475                 480
Val Asp Gly Leu Ser Val Asn Leu Tyr Tyr Glu Glu Gly Val Leu Val
                485                 490                 495
Tyr Gly Ala Thr Arg Gly Asp Gly Glu Val Gly Glu Glu Val Thr Gln
                500                 505                 510
Asn Leu Leu Thr Ile Pro Thr Ile Pro Arg Arg Leu Lys Gly Val Pro
            515                 520                 525
Glu Arg Leu Glu Val Arg Gly Glu Val Tyr Met Pro Ile Glu Ala Phe
            530                 535                 540
Leu Arg Leu Asn Glu Glu Leu Glu Glu Arg Gly Glu Arg Ile Phe Lys
545                 550                 555                 560
Asn Pro Arg Asn Ala Ala Ala Gly Ser Leu Arg Gln Lys Asp Pro Arg
                565                 570                 575
Ile Thr Ala Lys Arg Gly Leu Arg Ala Thr Phe Tyr Ala Leu Gly Leu
                580                 585                 590
Gly Leu Glu Glu Val Glu Arg Gly Val Ala Thr Gln Phe Ala Leu
            595                 600                 605
```

```
Leu His Trp Leu Lys Glu Lys Gly Phe Pro Val Glu His Gly Tyr Ala
    610                 615                 620

Arg Ala Val Gly Ala Glu Gly Val Glu Ala Val Tyr Gln Asp Trp Leu
625                 630                 635                 640

Lys Lys Arg Arg Ala Leu Pro Phe Glu Ala Asp Gly Val Val Lys
                645                 650                 655

Leu Asp Glu Leu Ala Leu Trp Arg Glu Leu Gly Tyr Thr Ala Arg Ala
                660                 665                 670

Pro Arg Phe Ala Ile Ala Tyr Lys Phe Pro Ala Glu Glu Lys Glu Thr
            675                 680                 685

Arg Leu Leu Asp Val Val Phe Gln Val Gly Arg Thr Gly Arg Val Thr
690                 695                 700

Pro Val Gly Ile Leu Glu Pro Val Phe Leu Glu Gly Ser Glu Val Ser
705                 710                 715                 720

Arg Val Thr Leu His Asn Glu Ser Tyr Ile Glu Glu Leu Asp Ile Arg
                725                 730                 735

Ile Gly Asp Trp Val Leu Val His Lys Ala Gly Gly Val Ile Pro Glu
            740                 745                 750

Val Leu Arg Val Leu Lys Glu Arg Arg Thr Gly Glu Glu Arg Pro Ile
    755                 760                 765

Arg Trp Pro Glu Thr Cys Pro Glu Cys Gly His Arg Leu Leu Lys Glu
770                 775                 780

Gly Lys Val His Arg Cys Pro Asn Pro Leu Cys Pro Ala Lys Arg Phe
785                 790                 795                 800

Glu Ala Ile Arg His Phe Ala Ser Arg Lys Ala Met Asp Ile Gln Gly
                805                 810                 815

Leu Gly Glu Lys Leu Ile Glu Arg Leu Leu Lys Gly Leu Val Lys
            820                 825                 830

Asp Val Ala Asp Leu Tyr Arg Leu Arg Lys Glu Asp Leu Val Gly Leu
    835                 840                 845

Glu Arg Met Gly Glu Lys Ser Ala Gln Asn Leu Leu Arg Gln Ile Glu
850                 855                 860

Glu Ser Lys Lys Arg Gly Leu Glu Arg Leu Leu Tyr Ala Leu Gly Leu
865                 870                 875                 880

Pro Gly Val Gly Glu Val Leu Ala Arg Asn Leu Ala Ala Arg Phe Gly
                885                 890                 895

Asn Met Asp Arg Leu Leu Glu Ala Ser Leu Glu Glu Leu Leu Glu Val
            900                 905                 910

Glu Glu Val Gly Glu Leu Thr Ala Arg Ala Ile Leu Glu Thr Leu Lys
    915                 920                 925

Asp Pro Ala Phe Arg Asp Leu Val Arg Arg Leu Lys Glu Ala Gly Val
930                 935                 940

Glu Met Glu Ala Lys Glu Lys Gly Gly Glu Ala Leu Lys Gly Leu Thr
945                 950                 955                 960

Phe Val Ile Thr Gly Glu Leu Ser Arg Pro Arg Glu Glu Val Lys Ala
                965                 970                 975

Leu Leu Arg Arg Leu Gly Ala Lys Val Thr Asp Ser Val Ser Arg Lys
            980                 985                 990

Thr Ser Tyr Leu Val Val Gly Glu Asn Pro Gly Ser Lys Leu Glu Lys
    995                 1000                1005

Ala Arg Ala Leu Gly Val Pro Thr Leu Thr Glu Glu Glu Leu Tyr
    1010                1015                1020
```

Arg Leu Leu Glu Ala Arg Thr Gly Lys Lys Ala Glu Glu Leu Val
    1025                1030                1035

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggatcatca tccaagtact tggatgatga tccc                                34

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aattctcttt aaataaaccc a                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacacaatct gcatgaaatc                                                20

<210> SEQ ID NO 5
<211> LENGTH: 334
<212> TYPE: DNA
<213> ORGANISM: Chlamydophila pneumoniae

<400> SEQUENCE: 5
aattctcttt aaataaaccc aagggctata aaggcgttgc tttcccttg ccaacagatg     60 ctggcgtagt aacagctgct ggaacaaagt ctgcgaccat caattatcat gaatggcagg   120
taggagcctc tctatcttat agactcaact ctttagtgcc atacattgga gtccaatggt   180
ctcgagcaac ttttgatgct gataacatcc gcattgctca gccaaagcta cctacagcta   240
ttttaaactt aactgcatgg aaccttcttt tactagggag tgccacagct gtttcttcat   300
ctgatcaatt ctcagatttc atgcagattg tgtc                               334

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacacaatct gcatgaaatc                                                20

<210> SEQ ID NO 7
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 7
gacacaatct gcatgaaatc                                              20

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggatcatca gcctagaaaa aaaaaaaaaa aaaagtact taaaaaaaat aggctgatga    60
tccc                                                               64

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggatcatca tcacatagta ctatgtgatg atgatccc                          38

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggatcatca tccatcagta ctgatggatg atgatccc                          38

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggatcatca gcctagtcag tcagtcattc attcagtact tcagtcagtt aggctgatga   60
tccc                                                               64

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 12

His His His His His His His His His His
1               5                   10
```